United States Patent [19]
Swaminathan et al.

[11] Patent Number: 5,830,714
[45] Date of Patent: Nov. 3, 1998

[54] BIOLOGICALLY ACTIVE FRAGMENT OF *BACILLUS STEAROTHERMOPHILUS* DNA POLYMERASE

[75] Inventors: Neela Swaminathan, Madison; Richard K. Wilkosz, New Berlin, both of Wis.

[73] Assignee: Molecular Biology Resources, Inc., Milwaukee, Wis.

[21] Appl. No.: 633,476

[22] Filed: Apr. 17, 1996

[51] Int. Cl.$^6$ .............. C12N 9/12; C12N 15/54; C12P 19/34
[52] U.S. Cl. .............. 435/91.2; 435/194; 435/320.1; 435/252.3; 435/325; 435/419; 536/23.2
[58] Field of Search .................. 435/194, 91.2, 435/320.1, 252.3, 325, 419; 536/23.2

[56] References Cited

U.S. PATENT DOCUMENTS 5,436,326  7/1995  Ishino et al. .......................... 536/23.2

OTHER PUBLICATIONS

Phang et al., *Gene,* (1995) vol. 163:65–68.
Kabov et al., *J. Bact.,* Jan. 1981, 145(1):21–26.

*Primary Examiner*—Keith D. Hendricks
*Attorney, Agent, or Firm*—Marshall, O'Toole, Gerstein, Murray & Borun

[57] ABSTRACT

The present invention is directed to an isolated and purified DNA encoding a biologically active fragment of a thermostable, full length DNA polymerase I enzyme of *Bacillus stearothermophilus*. More particularly, the invention is directed to a DNA encoding an approximately 66,000 dalton DNA polymerase that lacks 273 amino acids from the N-terminus of the approximately 96,000 dalton *B. stearothermophilus* DNA polymerase I, and to the protein encoded thereby which has been designated the *B. stearothermophilus* DNA polymerase I exo- fragment. The enzyme fragments are useful in DNA sequencing, cDNA preparations, thermophilic Strand Displacement Amplification and other molecular biology applications.

23 Claims, 16 Drawing Sheets

FIGURE 2a-I

*GTCGACAAGGCGCGCAGCCGCGATTCCGGCGGAACGGGGTTGGGCCTGG*
*CGATTGTGAAACATTTGGTTGAGGCTCACCATGGATATATTACCGTAGCGAG*
*CAAAGTGGGGCGCGGCACCGTGTTCACGATCCATTTTCCAAAGCCGGGGC*
*GGTAGCCGGCTTCTTTTGATCATCTCCAACTGAGAAGCCTCCCATTTTTCAG*
*CGTGAGCGTAAGCAGGGGATGAATCGGCGCCTCCCATCATGGTGGGAGAG*
*CGTTCAAGGCAAGCCGCAGGCATGGTACAATAGGACAAGGAAGCATCCGA*
*GGAGGGATGAGA*

TTGAAAAAAAGCTTGTTTTAATCGACGGCAGCAGCGTGGCGTA
CCGCGCCTTTTTGCCTTGCCGCTTTTGCATAACGACAAAGGCATCCA
TACGAACGCCGTCTACGGGTTTACGATGATGTTGAATAAAATTTTGGC
GGAAGAAGAGCCAACTCATATGCTTGTCGCGTTTGACGCCGGGAAAA
CGACGTTCCGGCATGAAGCGTTTCAAGAGTATAAAGGTGGGCGCCAG
CAGACGCCACCGGAGCTGTCGGAGCAGTTTCCGCTGTTGCGCGAGCT
GCTGAGGGCGTATCGCATCCCCGCCATGAACTCGAGAACTACGAAG
CGGACGATATTATCGGAACGCTTGCCGCCCGCGCTGAGCAGGAAGGG
TTTGAGATGAAAGTCATTTCCGGCGACCGCGATCTGACCCAGCTCGC
CTCCCCCCATGTGACGGTGGACATTACGAAAAAGGGATTACCGATA
TCGAACCATACACGCCGGAGACGGTCCGCGAAAAATACGGCTTAACT
CCGGAACAAATCGTTGATTTGAAAGGATTGATGGGCGACAAATCGGA
CAACATCCCCGGAGTGCCGGGCATCGGGGAAAAGACGGCGGTCAAGC
TGCTCAGGCAATTCGGCACGGTCGAAATGTGCTTGCCTCCATTGAC
GAGATCAAAGGCGAAAAGTTGAAAGAAACGCTGCGCCAACACCGGG
AGATGGCGCTGTTAAGCAAAAAGCTCGCCGCCATTCGCCGCGACGCC
CCGGTCGAGCTCTCGCTTGATGACATCGCCTATCAAGGGGAAGACCG
GGAGAAAGTGGTCGCTTTATTTAAAGAGCTTGGGTTTCAATCGTTTTA
GAGAAA

ATGGAATCGCCGTCATCAGAAGAGGAAAAACCGCTTGCCAAGA
TGGCATTTACGCTTGCTGACCGCGTGACGGAGGAGATGCTTGCC
GACAAGGCGGCGCTTGTCGTTGAAGTGGTCGAGGAAAATTATCATGAT
GCGCCGATCGTCGGCATCGCTGTGGTCAACGAACATGGACGGTTTTC
CTGCGCCCGGAGACGGCGCTTGCCGATCCGCAGTTTGTCGCCTGGCTT
GGTGATGAAACGAAGAAAAAAGCATGTTTGACTCAAAGCGCGCGGC
AGTCGCCTTGAAATGGAAGGAATTGAGCTATGCGGCGTTTCCTTTGATTTATTG
CTGGC

FIGURE 2a-II

CGCCTATTTGCTTGATCCGGCGCAAGGTGTTGATGATGTGGCTGCCGC
AGCAAAAATGAAGCAATACGAAGCGGTGCGCCCGGATGAAGCGGTGT
ATGGCAAGGGGCGAAGCGGGCCGTGCCGGATGAGCCAGTGCTCGCC
GAGCATTTGGTCCGCAAGGCGGCGGCGATTTGGGCGCTCGAACGGCC
GTTTTTGGATGAGCTGCGCCGCAACGAACAAGATCGGTTGCTCGTCG
AGCTCGAGCAGCCGTTGTCTTCGATTTTGGCGGAAATGGAATTTGCCG
GAGTGAAAGTGGATACGAAGCGGCTCGAACAGATGGGCGAAGAGCT
CGCCGAGCAGCTGCGCACGGTCGAGCAGCGCATTTATGAGCTCGCCG
GCCAAGAATTCAACATCAATTCACCGAAACAGCTCGGCGTCATTTTA
TTTGAAAAACTGCAGCTGCCCGTCTTGAAAAAACGAAAACCGGCTA
CTCCACTTCGGCGGATGTGCTTGAAAAACTTGCGCCTTATCACGAGAT
CGTGGAAAACATTTTGCATTACCGCCAGCTTGGCAAGTTGCAGTCGA
CGTATATTGAAGGATTGCTGAAAGTCGTGCGACCCGATACAAAGAAG
GTGCATACGATTTTCAATCAGGCGTTGACGCAAACCGGACGGCTCAG
CTCGACGGAGCCGAACTTGCAAACATTCCGATTCGGCTTGAGGAAG
GACGGAAAATCCGCCAAGCGTTCGTGCCATCGGAGTCTGATTGGCTC
ATTTTCGCCGCCGACTACTCGCAAATTGAGTTGCGCGTCCTCGCCCAT
ATTGCGGAAGATGACAATTTAATGGAAGCGTTCCGCCGCGATTTGGA
TATCCATACGAAAACAGCGATGGACATTTTCCAAGTGAGCGAGGACG
AAGTGACGCCCAACATGCGCCGTCAGGCGAAGGCGGTCAACTTTGGG
ATCGTTTACGGGATCAGTGATTACGGCTTGGCGCAAAACTTAAATATT
TCGCGCAAAGAGGCGGCTGAATTCATCGAGCGCTACTTCGAAAGCTT
CCCTGGCGTGAAGCGGTATATGGAAAACATTGTGCAAGAA<u>GCAAAAC</u>
<u>AGAAAGGGTATGTGACGACGCTGCTGCATCGGCGCCGCTATTTGCCG</u>
<u>GATATCACGAGCCGCAACTTCAACGTCCGCAGCTTTGCTGAACGGAT</u>
<u>GGCGATGAACACGCCGATTCAAGGGAGCGCCGCTGACATTATTAAAA</u>
<u>AGGCGATGATCGATCTGAACGCCAGACTGAAGGAAGAGCGGCTGCAA</u>
<u>GCGCGCCTTTTGCTGCAGGTGCATGACGAGCTCATTTGGAGGCGCC</u>
GAAAGAAGAGATGGAGCGGCTGTGCCGGCTCGTTCCGGAAGTGATGG
AGCAAGCGGTCACACTTCGCGTGCCGCTCAAAGTCGATTACCATTAT
GGCTCGACGTGGTATGATGCGAAATAA
*AGAGAAGTCTTGGTGTGGAGCGCCGGCATCCCTAAGAAGGCCTGTGATGG*
*AATGAAAAAGCAGTTTCACAACGACTCTTCTCCAGTTGGGAAGCCTTGAACA*

FIGURE 2a-III

TCGAGCCGTCCTTCTCAACCAACATGACCGATTTTGTGAAAATCAGCGTTTC
TCACCGGCCTTTTAGGCAGAATCTTTCGGTGCGACGATTCTCGGCTGCGGG
TCGATGAATTGGAGCGAAACAGCTGCCGCCCCATGGAGAATCTTTCTCTCG
GCGGATGAACCGGCGTCAATGTGAAAGCGTCGGCGGGAACGATGCAGGAA
AACGGAGGAAAGGGGGGATCCGAATTCGTTCCCTTTAGTGAGGGTTAATTC
CCGGCCGCGTCGAC

LKKKLVLIDGSSVAYRAFFALPLLHNDKGIHTNAVYGFTMMLNKILAEE
EPTHMLVAFDAGKTTFRHEAFQEYKGGRQQTPPELSEQFPLLRELLRAY
RIPAYELENYEADDIIGTLAARAEQEGFEMKVISGDRDLTQLASPHVTVDI
TKKGITDIEPYTPETVREKYGLTPEQIVDLKGLMGDKSDNIPGVPGIGEKT
AVKLLRQFGTVENVLASIDEIKGEKLKETLRQHREMALLSKKLAAIRRDA
PVELSLDDIAYQGEDREKVVALFKELGFQSFLEK
MESPSSEEEKPLAKMAFTLADRVTEEMLADKAALVVEVVEENYHDAPI
VGIAVVNEHGRFFLRPETALADPQFVAWLGDETKKKSMFDSKRAAVAL
KWKGIELCGVSFDLLLAAYLLDPAQGVDDVAAAAKMKQYEAVRPDEA
VYGKGAKRAVPDEPVLAEHLVRKAAAIWALERPFLDELRRNEQDRLLV
ELEQPLSSILAEMEFAGVKVDTKRLEQMGEELAEQLRTVEQRIYELAGQE
FNINSPKQLGVILFEKLQLPVLKKTKTGYSTSADVLEKLAPYHEIVENILH
YRQLGKLQSTYIEGLLKVVRPDTKKVHTIFNQALTQTGRLSSTEPNLQNIP
IRLEEGRKIRQAFVPSESDWLIFAADYSQIELRVLAHIAEDDNLMEAFRRD
LDIHTKTAMDIFQVSEDEVTPNMRRQAKAVNFGIVYGISDYGLAQNLNIS
RKEAAEFIERYFESFPGVKRYMENIVQEAKQKGYVTTLLHRRRYLPDITS
RNFNVRSFAERMAMNTPIQGSAADIIKKAMIDLNARLKEERLQARLLLQ
VHDELILEAPKEEMERLCRLVPEVMEQAVTLRVPLKVDYHYGSTWYDA
K*

FIGURE 2b

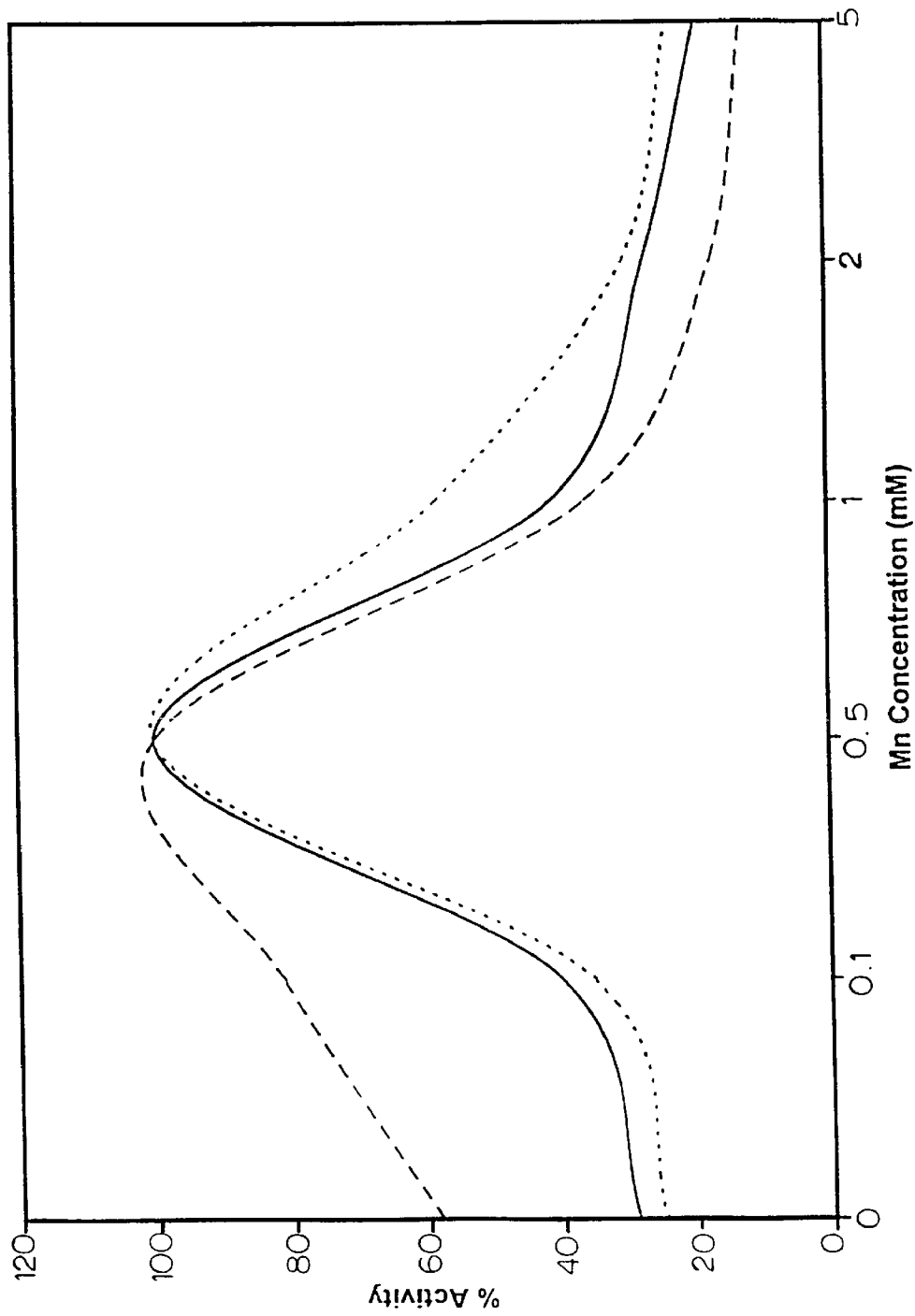

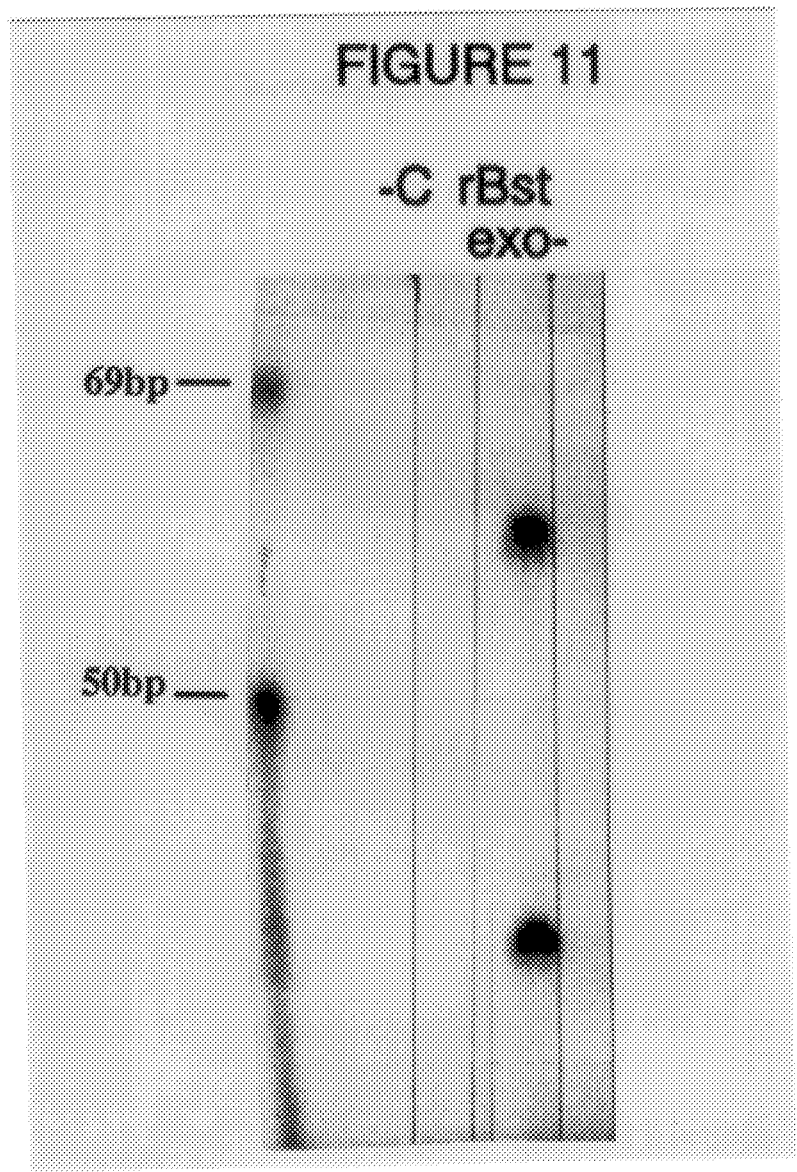

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3317 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 316..2943

( x i ) SEQUENCE DESCRIPTION: SEQ ID NO:1:

```
GTCGACAAGG  CGCGCAGCCG  CGATTCCGGC  GGAACGGGGT  TGGGCCTGGC  GATTGTGAAA        60

CATTTGGTTG  AGGCTCACCA  TGGATATATT  ACCGTAGCGA  GCAAAGTGGG  GCGCGGCACC       120

GTGTTCACGA  TCCATTTTCC  AAAGCCGGGG  CGGTAGCCGG  CTTCTTTTGA  TCATCTCCAA       180

CTGAGAAGCC  TCCCATTTTT  CAGCGTGAGC  GTAAGCAGGG  GATGAATCGG  CGCCTCCCAT       240

CATGGTGGGA  GAGCGTTCAA  GGCAAGCCGC  AGGCATGGTA  CAATAGGACA  AGGAAGCATC       300

CGAGGAGGGA  TGAGA  TTG  AAA  AAA  AAG  CTT  GTT  TTA  ATC  GAC  GGC  AGC  AGC       351
                    Leu  Lys  Lys  Lys  Leu  Val  Leu  Ile  Asp  Gly  Ser  Ser
                     1                 5                          10

GTG  GCG  TAC  CGC  GCC  TTT  TTT  GCC  TTG  CCG  CTT  TTG  CAT  AAC  GAC  AAA       399
Val  Ala  Tyr  Arg  Ala  Phe  Phe  Ala  Leu  Pro  Leu  Leu  His  Asn  Asp  Lys
              15                      20                      25

GGC  ATC  CAT  ACG  AAC  GCC  GTC  TAC  GGG  TTT  ACG  ATG  ATG  TTG  AAT  AAA       447
Gly  Ile  His  Thr  Asn  Ala  Val  Tyr  Gly  Phe  Thr  Met  Met  Leu  Asn  Lys
      30                      35                      40

ATT  TTG  GCG  GAA  GAA  GAG  CCA  ACT  CAT  ATG  CTT  GTC  GCG  TTT  GAC  GCC       495
Ile  Leu  Ala  Glu  Glu  Glu  Pro  Thr  His  Met  Leu  Val  Ala  Phe  Asp  Ala
 45                      50                      55                      60

GGG  AAA  ACG  ACG  TTC  CGG  CAT  GAA  GCG  TTT  CAA  GAG  TAT  AAA  GGT  GGG       543
Gly  Lys  Thr  Thr  Phe  Arg  His  Glu  Ala  Phe  Gln  Glu  Tyr  Lys  Gly  Gly
                      65                      70                      75

CGC  CAG  CAG  ACG  CCA  CCG  GAG  CTG  TCG  GAG  CAG  TTT  CCG  CTG  TTG  CGC       591
Arg  Gln  Gln  Thr  Pro  Pro  Glu  Leu  Ser  Glu  Gln  Phe  Pro  Leu  Leu  Arg
               80                      85                      90

GAG  CTG  CTG  AGG  GCG  TAT  CGC  ATC  CCC  GCC  TAT  GAA  CTC  GAG  AAC  TAC       639
Glu  Leu  Leu  Arg  Ala  Tyr  Arg  Ile  Pro  Ala  Tyr  Glu  Leu  Glu  Asn  Tyr
           95                      100                     105

GAA  GCG  GAC  GAT  ATT  ATC  GGA  ACG  CTT  GCC  GCC  CGC  GCT  GAG  CAG  GAA       687
Glu  Ala  Asp  Asp  Ile  Ile  Gly  Thr  Leu  Ala  Ala  Arg  Ala  Glu  Gln  Glu
       110                     115                     120

GGG  TTT  GAG  ATG  AAA  GTC  ATT  TCC  GGC  GAC  CGC  GAT  CTG  ACC  CAG  CTC       735
Gly  Phe  Glu  Met  Lys  Val  Ile  Ser  Gly  Asp  Arg  Asp  Leu  Thr  Gln  Leu
125                     130                     135                     140

GCC  TCC  CCC  CAT  GTG  ACG  GTG  GAC  ATT  ACG  AAA  AAA  GGG  ATT  ACC  GAT       783
Ala  Ser  Pro  His  Val  Thr  Val  Asp  Ile  Thr  Lys  Lys  Gly  Ile  Thr  Asp
                      145                     150                     155

ATC  GAA  CCA  TAC  ACG  CCG  GAG  ACG  GTC  CGC  GAA  AAA  TAC  GGC  TTA  ACT       831
```

| | | | | | | | | | | | | | | | | |
|---|---|---|---|---|---|---|---|---|---|---|---|---|---|---|---|---|
| Ile | Glu | Pro | Tyr | Thr | Pro | Glu | Thr | Val | Arg | Glu | Lys | Tyr | Gly | Leu | Thr | |
| | | | 160 | | | | 165 | | | | | | 170 | | | |
| CCG | GAA | CAA | ATC | GTT | GAT | TTG | AAA | GGA | TTG | ATG | GGC | GAC | AAA | TCG | GAC | 879 |
| Pro | Glu | Gln | Ile | Val | Asp | Leu | Lys | Gly | Leu | Met | Gly | Asp | Lys | Ser | Asp | |
| | | 175 | | | | 180 | | | | | 185 | | | | | |
| AAC | ATC | CCC | GGA | GTG | CCG | GGC | ATC | GGG | GAA | AAG | ACG | GCG | GTC | AAG | CTG | 927 |
| Asn | Ile | Pro | Gly | Val | Pro | Gly | Ile | Gly | Glu | Lys | Thr | Ala | Val | Lys | Leu | |
| | 190 | | | | | 195 | | | | | 200 | | | | | |
| CTC | AGG | CAA | TTC | GGC | ACG | GTC | GAA | AAT | GTG | CTT | GCC | TCC | ATT | GAC | GAG | 975 |
| Leu | Arg | Gln | Phe | Gly | Thr | Val | Glu | Asn | Val | Leu | Ala | Ser | Ile | Asp | Glu | |
| 205 | | | | | 210 | | | | | 215 | | | | | 220 | |
| ATC | AAA | GGC | GAA | AAG | TTG | AAA | GAA | ACG | CTG | CGC | CAA | CAC | CGG | GAG | ATG | 1023 |
| Ile | Lys | Gly | Glu | Lys | Leu | Lys | Glu | Thr | Leu | Arg | Gln | His | Arg | Glu | Met | |
| | | | | 225 | | | | 230 | | | | | | 235 | | |
| GCG | CTG | TTA | AGC | AAA | AAG | CTC | GCC | GCC | ATT | CGC | CGC | GAC | GCC | CCG | GTC | 1071 |
| Ala | Leu | Leu | Ser | Lys | Lys | Leu | Ala | Ala | Ile | Arg | Arg | Asp | Ala | Pro | Val | |
| | | | 240 | | | | 245 | | | | | 250 | | | | |
| GAG | CTC | TCG | CTT | GAT | GAC | ATC | GCC | TAT | CAA | GGG | GAA | GAC | CGG | GAG | AAA | 1119 |
| Glu | Leu | Ser | Leu | Asp | Asp | Ile | Ala | Tyr | Gln | Gly | Glu | Asp | Arg | Glu | Lys | |
| | | 255 | | | | 260 | | | | | 265 | | | | | |
| GTG | GTC | GCT | TTA | TTT | AAA | GAG | CTT | GGG | TTT | CAA | TCG | TTT | TTA | GAG | AAA | 1167 |
| Val | Val | Ala | Leu | Phe | Lys | Glu | Leu | Gly | Phe | Gln | Ser | Phe | Leu | Glu | Lys | |
| 270 | | | | | 275 | | | | | 280 | | | | | | |
| ATG | GAA | TCG | CCG | TCA | TCA | GAA | GAG | GAA | AAA | CCG | CTT | GCC | AAG | ATG | GCA | 1215 |
| Met | Glu | Ser | Pro | Ser | Ser | Glu | Glu | Glu | Lys | Pro | Leu | Ala | Lys | Met | Ala | |
| 285 | | | | | 290 | | | | | 295 | | | | | 300 | |
| TTT | ACG | CTT | GCT | GAC | CGC | GTG | ACG | GAG | GAG | ATG | CTT | GCC | GAC | AAG | GCG | 1263 |
| Phe | Thr | Leu | Ala | Asp | Arg | Val | Thr | Glu | Glu | Met | Leu | Ala | Asp | Lys | Ala | |
| | | | | 305 | | | | 310 | | | | | | 315 | | |
| GCG | CTT | GTC | GTT | GAA | GTG | GTC | GAG | GAA | AAT | TAT | CAT | GAT | GCG | CCG | ATC | 1311 |
| Ala | Leu | Val | Val | Glu | Val | Val | Glu | Glu | Asn | Tyr | His | Asp | Ala | Pro | Ile | |
| | | | 320 | | | | 325 | | | | | 330 | | | | |
| GTC | GGC | ATC | GCT | GTG | GTC | AAC | GAA | CAT | GGA | CGG | TTT | TTC | CTG | CGC | CCG | 1359 |
| Val | Gly | Ile | Ala | Val | Val | Asn | Glu | His | Gly | Arg | Phe | Phe | Leu | Arg | Pro | |
| | | 335 | | | | 340 | | | | | 345 | | | | | |
| GAG | ACG | GCG | CTT | GCC | GAT | CCG | CAG | TTT | GTC | GCC | TGG | CTT | GGT | GAT | GAA | 1407 |
| Glu | Thr | Ala | Leu | Ala | Asp | Pro | Gln | Phe | Val | Ala | Trp | Leu | Gly | Asp | Glu | |
| 350 | | | | | 355 | | | | | 360 | | | | | | |
| ACG | AAG | AAA | AAA | AGC | ATG | TTT | GAC | TCA | AAG | CGC | GCG | GCA | GTC | GCC | TTG | 1455 |
| Thr | Lys | Lys | Lys | Ser | Met | Phe | Asp | Ser | Lys | Arg | Ala | Ala | Val | Ala | Leu | |
| 365 | | | | | 370 | | | | | 375 | | | | | 380 | |
| AAA | TGG | AAA | GGA | ATT | GAG | CTA | TGC | GGC | GTT | TCC | TTT | GAT | TTA | TTG | CTG | 1503 |
| Lys | Trp | Lys | Gly | Ile | Glu | Leu | Cys | Gly | Val | Ser | Phe | Asp | Leu | Leu | Leu | |
| | | | | 385 | | | | 390 | | | | | 395 | | | |
| GCC | GCC | TAT | TTG | CTT | GAT | CCG | GCG | CAA | GGT | GTT | GAT | GAT | GTG | GCT | GCC | 1551 |
| Ala | Ala | Tyr | Leu | Leu | Asp | Pro | Ala | Gln | Gly | Val | Asp | Asp | Val | Ala | Ala | |
| | | | 400 | | | | 405 | | | | | 410 | | | | |
| GCA | GCA | AAA | ATG | AAG | CAA | TAC | GAA | GCG | GTG | CGC | CCG | GAT | GAA | GCG | GTG | 1599 |
| Ala | Ala | Lys | Met | Lys | Gln | Tyr | Glu | Ala | Val | Arg | Pro | Asp | Glu | Ala | Val | |
| | | 415 | | | | 420 | | | | | 425 | | | | | |
| TAT | GGC | AAA | GGG | GCG | AAG | CGG | GCC | GTG | CCG | GAT | GAG | CCA | GTG | CTC | GCC | 1647 |
| Tyr | Gly | Lys | Gly | Ala | Lys | Arg | Ala | Val | Pro | Asp | Glu | Pro | Val | Leu | Ala | |
| | 430 | | | | 435 | | | | | 440 | | | | | | |
| GAG | CAT | TTG | GTC | CGC | AAG | GCG | GCG | GCG | ATT | TGG | GCG | CTC | GAA | CGG | CCG | 1695 |
| Glu | His | Leu | Val | Arg | Lys | Ala | Ala | Ala | Ile | Trp | Ala | Leu | Glu | Arg | Pro | |
| 445 | | | | 450 | | | | | 455 | | | | | | 460 | |
| TTT | TTG | GAT | GAG | CTG | CGC | CGC | AAC | GAA | CAA | GAT | CGG | TTG | CTC | GTC | GAG | 1743 |
| Phe | Leu | Asp | Glu | Leu | Arg | Arg | Asn | Glu | Gln | Asp | Arg | Leu | Leu | Val | Glu | |
| | | | | 465 | | | | 470 | | | | | 475 | | | |
| CTC | GAG | CAG | CCG | TTG | TCT | TCG | ATT | TTG | GCG | GAA | ATG | GAA | TTT | GCC | GGA | 1791 |

| | | | | | | | | | | | | | | | | |
|---|---|---|---|---|---|---|---|---|---|---|---|---|---|---|---|---|
| Leu | Glu | Gln | Pro 480 | Leu | Ser | Ser | Ile | Leu 485 | Ala | Glu | Met | Glu | Phe 490 | Ala | Gly | |
| GTG Val | AAA Lys | GTG Val 495 | GAT Asp | ACG Thr | AAG Lys | CGG Arg | CTC Leu | GAA Glu 500 | CAG Gln | ATG Met | GGC Gly | GAA Glu | GAG Glu 505 | CTC Leu | GCC Ala | 1839 |
| GAG Glu | CAG Gln | CTG Leu 510 | CGC Arg | ACG Thr | GTC Val | GAG Glu | CAG Gln 515 | CGC Arg | ATT Ile | TAT Tyr | GAG Glu | CTC Leu 520 | GCC Ala | GGC Gly | CAA Gln | 1887 |
| GAA Glu 525 | TTC Phe | AAC Asn | ATC Ile | AAT Asn | TCA Ser 530 | CCG Pro | AAA Lys | CAG Gln | CTC Leu | GGC Gly 535 | GTC Val | ATT Ile | TTA Leu | TTT Phe | GAA Glu 540 | 1935 |
| AAA Lys | CTG Leu | CAG Gln | CTG Leu | CCC Pro 545 | GTC Val | TTG Leu | AAA Lys | AAA Lys | ACG Thr 550 | AAA Lys | ACC Thr | GGC Gly | TAC Tyr | TCC Ser 555 | ACT Thr | 1983 |
| TCG Ser | GCG Ala | GAT Asp | GTG Val 560 | CTT Leu | GAA Glu | AAA Lys | CTT Leu | GCG Ala 565 | CCT Pro | TAT Tyr | CAC His | GAG Glu | ATC Ile 570 | GTG Val | GAA Glu | 2031 |
| AAC Asn | ATT Ile | TTG Leu 575 | CAT His | TAC Tyr | CGC Arg | CAG Gln | CTT Leu 580 | GGC Gly | AAG Lys | TTG Leu | CAG Gln | TCG Ser 585 | ACG Thr | TAT Tyr | ATT Ile | 2079 |
| GAA Glu | GGA Gly 590 | TTG Leu | CTG Leu | AAA Lys | GTC Val | GTG Val 595 | CGA Arg | CCC Pro | GAT Asp | ACA Thr | AAG Lys 600 | AAG Lys | GTG Val | CAT His | ACG Thr | 2127 |
| ATT Ile 605 | TTC Phe | AAT Asn | CAG Gln | GCG Ala | TTG Leu 610 | ACG Thr | CAA Gln | ACC Thr | GGA Gly | CGG Arg 615 | CTC Leu | AGC Ser | TCG Ser | ACG Thr | GAG Glu 620 | 2175 |
| CCG Pro | AAC Asn | TTG Leu | CAA Gln | AAC Asn 625 | ATT Ile | CCG Pro | ATC Ile | CGG Arg | CTT Leu 630 | GAG Glu | GAA Glu | GGA Gly | CGG Arg | AAA Lys 635 | ATC Ile | 2223 |
| CGC Arg | CAA Gln | GCG Ala | TTC Phe 640 | GTG Val | CCA Pro | TCG Ser | GAG Glu | TCT Ser 645 | GAT Asp | TGG Trp | CTC Leu | ATT Ile | TTC Phe 650 | GCC Ala | GCC Ala | 2271 |
| GAC Asp | TAC Tyr | TCG Ser 655 | CAA Gln | ATT Ile | GAG Glu | TTG Leu | CGC Arg 660 | GTC Val | CTC Leu | GCC Ala | CAT His | ATT Ile 665 | GCG Ala | GAA Glu | GAT Asp | 2319 |
| GAC Asp | AAT Asn | TTA Leu 670 | ATG Met | GAA Glu | GCG Ala | TTC Phe | CGC Arg 675 | CGC Arg | GAT Asp | TTG Leu | GAT Asp | ATC Ile 680 | CAT His | ACG Thr | AAA Lys | 2367 |
| ACA Thr | GCG Ala | ATG Met 685 | GAC Asp | ATT Ile | TTC Phe | CAA Gln | GTG Val 690 | AGC Ser | GAG Glu | GAC Asp | GAA Glu | GTG Val 695 | ACG Thr | CCC Pro | AAC Asn 700 | 2415 |
| ATG Met | CGC Arg | CGT Arg | CAG Gln | GCG Ala 705 | AAG Lys | GCG Ala | GTC Val | AAC Asn | TTT Phe 710 | GGG Gly | ATC Ile | GTT Val | TAC Tyr | GGG Gly 715 | ATC Ile | 2463 |
| AGT Ser | GAT Asp | TAC Tyr | GGC Gly 720 | TTG Leu | GCG Ala | CAA Gln | AAC Asn | TTA Leu 725 | AAT Asn | ATT Ile | TCG Ser | CGC Arg | AAA Lys 730 | GAG Glu | GCG Ala | 2511 |
| GCT Ala | GAA Glu | TTC Phe 735 | ATC Ile | GAG Glu | CGC Arg | TAC Tyr | TTC Phe 740 | GAA Glu | AGC Ser | TTC Phe | CCT Pro | GGC Gly 745 | GTG Val | AAG Lys | CGG Arg | 2559 |
| TAT Tyr | ATG Met | GAA Glu 750 | AAC Asn | ATT Ile | GTG Val | CAA Gln | GAA Glu 755 | GCA Ala | AAA Lys | CAG Gln | AAA Lys | GGG Gly 760 | TAT Tyr | GTG Val | ACG Thr | 2607 |
| ACG Thr | CTG Leu 765 | CTG Leu | CAT His | CGG Arg | CGC Arg 770 | CGC Arg | TAT Tyr | TTG Leu | CCG Pro | GAT Asp 775 | ATC Ile | ACG Thr | AGC Ser | CGC Arg | AAC Asn 780 | 2655 |
| TTC Phe | AAC Asn | GTC Val | CGC Arg | AGC Ser 785 | TTT Phe | GCT Ala | GAA Glu | CGG Arg | ATG Met 790 | GCG Ala | ATG Met | AAC Asn | ACG Thr | CCG Pro 795 | ATT Ile | 2703 |
| CAA Gln | GGG Gly | AGC Ser | GCC Ala | GCT Ala | GAC Asp | ATT Ile | ATT Ile | AAA Lys | AAG Lys | GCG Ala | ATG Met | ATC Ile | GAT Asp | CTG Leu | AAC Asn | 2751 |

| Gln | Gly | Ser | Ala | Ala | Asp | Ile | Ile | Lys | Lys | Ala | Met | Ile | Asp | Leu | Asn | |
|-----|-----|-----|-----|-----|-----|-----|-----|-----|-----|-----|-----|-----|-----|-----|-----|---|
|     |     |     | 800 |     |     |     |     | 805 |     |     |     |     | 810 |     |     |   |

| GCC | AGA | CTG | AAG | GAA | GAG | CGG | CTG | CAA | GCG | CGC | CTT | TTG | CTG | CAG | GTG | 2799 |
|-----|-----|-----|-----|-----|-----|-----|-----|-----|-----|-----|-----|-----|-----|-----|-----|------|
| Ala | Arg | Leu | Lys | Glu | Glu | Arg | Leu | Gln | Ala | Arg | Leu | Leu | Leu | Gln | Val |      |
|     |     | 815 |     |     |     |     | 820 |     |     |     |     | 825 |     |     |     |      |

| CAT | GAC | GAG | CTC | ATT | TTG | GAG | GCG | CCG | AAA | GAA | GAG | ATG | GAG | CGG | CTG | 2847 |
|-----|-----|-----|-----|-----|-----|-----|-----|-----|-----|-----|-----|-----|-----|-----|-----|------|
| His | Asp | Glu | Leu | Ile | Leu | Glu | Ala | Pro | Lys | Glu | Glu | Met | Glu | Arg | Leu |      |
|     | 830 |     |     |     |     | 835 |     |     |     |     | 840 |     |     |     |     |      |

| TGC | CGG | CTC | GTT | CCG | GAA | GTG | ATG | GAG | CAA | GCG | GTC | ACA | CTT | CGC | GTG | 2895 |
|-----|-----|-----|-----|-----|-----|-----|-----|-----|-----|-----|-----|-----|-----|-----|-----|------|
| Cys | Arg | Leu | Val | Pro | Glu | Val | Met | Glu | Gln | Ala | Val | Thr | Leu | Arg | Val |      |
| 845 |     |     |     |     | 850 |     |     |     |     | 855 |     |     |     |     | 860 |      |

| CCG | CTC | AAA | GTC | GAT | TAC | CAT | TAT | GGC | TCG | ACG | TGG | TAT | GAT | GCG | AAA | 2943 |
|-----|-----|-----|-----|-----|-----|-----|-----|-----|-----|-----|-----|-----|-----|-----|-----|------|
| Pro | Leu | Lys | Val | Asp | Tyr | His | Tyr | Gly | Ser | Thr | Trp | Tyr | Asp | Ala | Lys |      |
|     |     |     |     | 865 |     |     |     |     | 870 |     |     |     |     | 875 |     |      |

| TAAAGAGAAG | TCTTGGTGTG | GAGCGCCGGC | ATCCCTAAGA | AGGCCTGTGA | TGGAATGAAA | 3003 |
|------------|------------|------------|------------|------------|------------|------|
| AAGCAGTTTC | ACAACGACTC | TTCTCCAGTT | GGGAAGCCTT | GAACATCGAG | CCGTCCTTCT | 3063 |
| CAACCAACAT | GACCGATTTT | GTGAAAATCA | GCGTTTCTCA | CCGGCCTTTT | AGGCAGAATC | 3123 |
| TTTCGGTGCG | ACGATTCTCG | GCTGCGGGTC | GATGAATTGG | AGCGAAACAG | CTGCCGCCCC | 3183 |
| ATGGAGAATC | TTTCTCTCGG | CGGATGAACC | GGCGTCAATG | TGAAAGCGTC | GGCGGGAACG | 3243 |
| ATGCAGGAAA | ACGGAGGAAA | GGGGGGATCC | GAATTCGTTC | CCTTTAGTGA | GGGTTAATTC | 3303 |
| CCGGCCGCGT | CGAC       |            |            |            |            | 3317 |

(2) INFORMATION FOR SEQ ID NO:2:

(i) SEQUENCE CHARACTERISTICS:
  (A) LENGTH: 876 amino acids
  (B) TYPE: amino acid
  (D) TOPOLOGY: linear (ii) MOLECULE TYPE: protein (xi) SEQUENCE DESCRIPTION: SEQ ID NO:2:

| Leu | Lys | Lys | Lys | Leu | Val | Leu | Ile | Asp | Gly | Ser | Ser | Val | Ala | Tyr | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Phe | Phe | Ala | Leu | Pro | Leu | Leu | His | Asn | Asp | Lys | Gly | Ile | His | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Ala | Val | Tyr | Gly | Phe | Thr | Met | Met | Leu | Asn | Lys | Ile | Leu | Ala | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Glu | Pro | Thr | His | Met | Leu | Val | Ala | Phe | Asp | Ala | Gly | Lys | Thr | Thr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Arg | His | Glu | Ala | Phe | Gln | Glu | Tyr | Lys | Gly | Gly | Arg | Gln | Gln | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Pro | Glu | Leu | Ser | Glu | Gln | Phe | Pro | Leu | Leu | Arg | Glu | Leu | Leu | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Tyr | Arg | Ile | Pro | Ala | Tyr | Glu | Leu | Glu | Asn | Tyr | Glu | Ala | Asp | Asp |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Ile | Gly | Thr | Leu | Ala | Ala | Arg | Ala | Glu | Gln | Glu | Gly | Phe | Glu | Met |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | Val | Ile | Ser | Gly | Asp | Arg | Asp | Leu | Thr | Gln | Leu | Ala | Ser | Pro | His |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Val | Thr | Val | Asp | Ile | Thr | Lys | Lys | Gly | Ile | Thr | Asp | Ile | Glu | Pro | Tyr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Thr | Pro | Glu | Thr | Val | Arg | Glu | Lys | Tyr | Gly | Leu | Thr | Pro | Glu | Gln | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Val | Asp | Leu | Lys | Gly | Leu | Met | Gly | Asp | Lys | Ser | Asp | Asn | Ile | Pro | Gly |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

-continued

| | | | | | | | | | | | | | | |
|---|---|---|---|---|---|---|---|---|---|---|---|---|---|---|
| Val | Pro | Gly 195 | Ile | Gly | Glu | Lys | Thr 200 | Ala | Val | Lys | Leu 205 | Leu | Arg | Gln | Phe |
| Gly | Thr 210 | Val | Glu | Asn | Val 215 | Leu | Ala | Ser | Ile | Asp 220 | Glu | Ile | Lys | Gly | Glu |
| Lys 225 | Leu | Lys | Glu | Thr | Leu 230 | Arg | Gln | His | Arg | Glu 235 | Met | Ala | Leu | Leu | Ser 240 |
| Lys | Lys | Leu | Ala | Ala 245 | Ile | Arg | Arg | Asp | Pro 250 | Val | Glu | Leu | Ser 255 | Leu |
| Asp | Asp | Ile | Ala 260 | Tyr | Gln | Gly | Glu | Asp 265 | Arg | Glu | Lys | Val 270 | Ala | Leu |
| Phe | Lys | Glu 275 | Leu | Gly | Phe | Gln | Ser 280 | Phe | Leu | Glu | Lys | Met 285 | Glu | Ser | Pro |
| Ser | Ser 290 | Glu | Glu | Glu | Lys | Pro 295 | Leu | Ala | Lys | Met | Ala 300 | Phe | Thr | Leu | Ala |
| Asp 305 | Arg | Val | Thr | Glu | Glu 310 | Met | Leu | Ala | Asp | Lys 315 | Ala | Ala | Leu | Val | Val 320 |
| Glu | Val | Val | Glu | Glu 325 | Asn | Tyr | His | Asp | Ala 330 | Pro | Ile | Val | Gly | Ile 335 | Ala |
| Val | Val | Asn | Glu 340 | His | Gly | Arg | Phe | Phe 345 | Leu | Arg | Pro | Glu | Thr 350 | Ala | Leu |
| Ala | Asp | Pro 355 | Gln | Phe | Val | Ala | Trp 360 | Leu | Gly | Asp | Glu | Thr 365 | Lys | Lys | Lys |
| Ser | Met 370 | Phe | Asp | Ser | Lys | Arg 375 | Ala | Ala | Val | Ala | Leu 380 | Lys | Trp | Lys | Gly |
| Ile 385 | Glu | Leu | Cys | Gly | Val 390 | Ser | Phe | Asp | Leu | Leu 395 | Leu | Ala | Ala | Tyr | Leu 400 |
| Leu | Asp | Pro | Ala | Gln 405 | Gly | Val | Asp | Asp | Val 410 | Ala | Ala | Ala | Lys 415 | Met |
| Lys | Gln | Tyr | Glu 420 | Ala | Val | Arg | Pro | Asp 425 | Glu | Ala | Val | Tyr | Gly 430 | Lys | Gly |
| Ala | Lys | Arg 435 | Ala | Val | Pro | Asp | Glu 440 | Pro | Val | Leu | Ala | Glu 445 | His | Leu | Val |
| Arg | Lys 450 | Ala | Ala | Ala | Ile | Trp 455 | Ala | Leu | Glu | Arg | Pro 460 | Phe | Leu | Asp | Glu |
| Leu 465 | Arg | Arg | Asn | Glu | Gln 470 | Asp | Arg | Leu | Leu | Val 475 | Glu | Leu | Glu | Gln | Pro 480 |
| Leu | Ser | Ser | Ile | Leu 485 | Ala | Glu | Met | Glu | Phe 490 | Ala | Gly | Val | Lys | Val 495 | Asp |
| Thr | Lys | Arg | Leu 500 | Glu | Gln | Met | Gly | Glu 505 | Glu | Leu | Ala | Glu | Gln 510 | Leu | Arg |
| Thr | Val | Glu 515 | Gln | Arg | Ile | Tyr | Glu 520 | Leu | Ala | Gly | Gln | Glu 525 | Phe | Asn | Ile |
| Asn | Ser 530 | Pro | Lys | Gln | Leu | Gly 535 | Val | Ile | Leu | Phe | Glu 540 | Lys | Leu | Gln | Leu |
| Pro 545 | Val | Leu | Lys | Lys | Thr 550 | Lys | Thr | Gly | Tyr | Ser 555 | Thr | Ser | Ala | Asp | Val 560 |
| Leu | Glu | Lys | Leu | Ala 565 | Pro | Tyr | His | Glu | Ile 570 | Val | Glu | Asn | Ile | Leu 575 | His |
| Tyr | Arg | Gln | Leu 580 | Gly | Lys | Leu | Gln | Ser 585 | Thr | Tyr | Ile | Glu | Gly 590 | Leu | Leu |
| Lys | Val | Val 595 | Arg | Pro | Asp | Thr | Lys 600 | Lys | Val | His | Thr | Ile 605 | Phe | Asn | Gln |
| Ala | Leu | Thr | Gln | Thr | Gly | Arg | Leu | Ser | Ser | Thr | Glu | Pro | Asn | Leu | Gln |

-continued

```
                    610                        615                         620
Asn  Ile  Pro  Ile  Arg  Leu  Glu  Glu  Gly  Arg  Lys  Ile  Arg  Gln  Ala  Phe
625                      630                       635                      640

Val  Pro  Ser  Glu  Ser  Asp  Trp  Leu  Ile  Phe  Ala  Ala  Asp  Tyr  Ser  Gln
                    645                       650                       655

Ile  Glu  Leu  Arg  Val  Leu  Ala  His  Ile  Ala  Glu  Asp  Asp  Asn  Leu  Met
               660                       665                       670

Glu  Ala  Phe  Arg  Arg  Asp  Leu  Asp  Ile  His  Thr  Lys  Thr  Ala  Met  Asp
               675                       680                       685

Ile  Phe  Gln  Val  Ser  Glu  Asp  Glu  Val  Thr  Pro  Asn  Met  Arg  Arg  Gln
          690                       695                       700

Ala  Lys  Ala  Val  Asn  Phe  Gly  Ile  Val  Tyr  Gly  Ile  Ser  Asp  Tyr  Gly
705                      710                       715                      720

Leu  Ala  Gln  Asn  Leu  Asn  Ile  Ser  Arg  Lys  Glu  Ala  Ala  Glu  Phe  Ile
                    725                       730                       735

Glu  Arg  Tyr  Phe  Glu  Ser  Phe  Pro  Gly  Val  Lys  Arg  Tyr  Met  Glu  Asn
               740                       745                       750

Ile  Val  Gln  Glu  Ala  Lys  Gln  Lys  Gly  Tyr  Val  Thr  Thr  Leu  Leu  His
          755                       760                       765

Arg  Arg  Arg  Tyr  Leu  Pro  Asp  Ile  Thr  Ser  Arg  Asn  Phe  Asn  Val  Arg
770                           775                       780

Ser  Phe  Ala  Glu  Arg  Met  Ala  Met  Asn  Thr  Pro  Ile  Gln  Gly  Ser  Ala
785                      790                       795                      800

Ala  Asp  Ile  Ile  Lys  Lys  Ala  Met  Ile  Asp  Leu  Asn  Ala  Arg  Leu  Lys
                    805                       810                       815

Glu  Glu  Arg  Leu  Gln  Ala  Arg  Leu  Leu  Leu  Gln  Val  His  Asp  Glu  Leu
               820                       825                       830

Ile  Leu  Glu  Ala  Pro  Lys  Glu  Glu  Met  Glu  Arg  Leu  Cys  Arg  Leu  Val
          835                       840                       845

Pro  Glu  Val  Met  Glu  Gln  Ala  Val  Thr  Leu  Arg  Val  Pro  Leu  Lys  Val
     850                       855                       860

Asp  Tyr  His  Tyr  Gly  Ser  Thr  Trp  Tyr  Asp  Ala  Lys
865                      870                       875
```

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

ATGAAAAAAA AGCTTGTTTT AATCGACGGC AGCAGCGTGG CG    42

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GCAAAACAGA AAGGGTATGT GACGAC    26

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

AAAATGAGCT CGTCATGCAC CTG          23

BIOLOGICALLY ACTIVE FRAGMENT OF BACILLUS STEAROTHERMOPHILUS DNA POLYMERASE

BACKGROUND OF THE INVENTION

A. Field of the Invention

The present invention relates to a thermostable recombinant protein fragment having DNA polymerase activity, 3'–5' exonuclease (proofreading) activity, reverse transcriptase activity and being substantially free of 5'–3' exonuclease activity. The thermostable recombinant polypeptide of the present invention is useful because it is capable of providing enhanced polymerase activity in bio-applications, such as in cDNA production, Strand Displacement Amplification and DNA sequencing.

B. Background

The field of biotechnology was revolutionized by recombinant DNA technology, and DNA polymerase enzymes have become an indispensable tool in many in vitro recombinant DNA biological applications such as DNA sequencing; Polymerase Chain Reaction (PCR) and its many variations (see, e.g., Erlich et al., Current Communications in Molecular Biology: Polymerase Chain Reaction. Cold Spring Harbor Laboratory Press, Cold Spring Harbor, N.Y. (1989); Innis et al., PCR protocols: A guide to methods and applications, Academic Press, San Diego, Calif. (1990)); Thermal Cycle Labeling (TCL) (Mead and Swaminathan, U.S. patent application Ser. No. 08/217,459, filed Mar. 24, 1994; PCT App. No. US94\03246, filed Mar. 24, 1994); Random Primer Labeling (RPL); Ligase Chain Reaction (LCR) (Wiedmann et al., PCR Methods and Applications 3: S51–S64 (1994)); Strand Displacement Amplification ("SDA") (Walker, T. G. Emperical Aspects of Strand Displacement Amplification, Becton Dickenson Research Center, Cold Spring Harbor Laboratory Press (1993)), and other applications.

To date, scientists have reported more than 40 different DNA polymerases. Comparisons of amino acid sequences has resulted in the placement of reported polymerase genes into four major families: namely, A, B, C, and X. Family A contains E. coli DNA polymerase I, an enzyme that is involved in repair of DNA and in replication during fast growth. Family B includes E. coli DNA polymerase II. Family C includes E. coli DNA polymerase III, the major replication enzyme. The fourth group, Family X, contains enzymes such as the eukaryotic DNA polymerase β and eukaryotic terminal transferases (Ito and Braithwaite, Nucleic Acids Res. 19: 4045–4057 (1991)).

DNA polymerase I (pol I) (Family A) enzymes have proved to be very useful for DNA sequencing applications, PCR, SDA, and other applications known in the art. Structure-function relationship studies indicate that the known DNA pol I molecules share a similar modular organization. A 5'–3' exonuclease function is located in the N-terminal one-third of the enzyme. The remainder of the molecule forms one domain which is further classified into functional sub-domains. Adjacent to the 5'–3' exonuclease domain lies a 3'–5' exonuclease sub-domain, followed by a polymerase sub-domain (Blanco et al., Gene 100: 27–38 (1991)).

In addition to classifying DNA polymerase enzymes into the above families, it is also useful to classify such polymerases as mesophilic (purified from mesophilic organisms) or thermophilic (purified from thermophilic organisms). (See, e.g., Bessman et al., J. Biol. Chem. 233: 171–177 (1958); Buttin and Kornberg, J. Biol. Chem. 241: 5419–5427 (1966); Uemori et al., Nucleic Acids Res. 21: 259–265 (1993); Lawyer et al. J. Biol. Chem. 264: 6427–6437 (1989); and Kaledin et al., Biokhimiya 45: 644–651 (1980)). The DNA polymerases of mesophilic origin are useful in many biological applications, such as in certain DNA sequencing applications. However, many important applications require thermal cycling to repeatedly denature template DNA and/or RNA and their extension products. Because the mesophilic DNA polymerases do not withstand the high temperatures or the thermal cycling of these applications, the thermostable DNA polymerases enjoy significant advantages over mesophilic DNA polymerases in such applications.

Through deletion of the 5' one-third of DNA polymerase I genes, or by the proteolytic cleavage and subsequent removal of the portion of the holoenzyme encoded thereby, scientists have created DNA pol I fragments retaining polymerizing activity, but having reduced 5'–3' exonuclease activity. (See, e.g., Joyce and Grindley, Proc. Natl. Acad. Sci. 80: 1830–1834 (1983) (the Klenow-Fragment of the E. coli DNA polymerase enzyme); Lawyer et al., J. Biol. Chem. 264: 6427–6437 (1989); Gelfand et al., U.S. Pat. No. 5,079, 352 (1992); Lawyer et al., PCR Methods and Applications 2 :275–287 (1993) (the Stoffel fragment of the T. aquaticus (Taq) DNA polymerase enzyme); and Barnes, Gene 112: 29–35 (1992) (the KlenTaq DNA polymerase).)

The different reports of thermostable DNA polymerases and their derivatives suggest these enzymes possess different, unpredictable properties that may be advantageous or detrimental, depending on the biological application in which the DNA polymerase is to be employed (Myers and Gelfand, Biochemistry 30: 7661–7666 (1991)). The KlenTaq DNA polymerase is an example of an enzyme fragment with important properties differing from the Taq holoenzyme. The KlenTaq DNA polymerase reportedly has roughly a two-fold lower PCR-induced relative mutation rate than Taq polymerase holoenzyme. However, more units of KlenTaq are needed to obtain PCR products similar to those generated with Taq DNA pol I. Similarly, Lawyer et al. (1993) reported that T. aquaticus DNA polymerase I fragments possessed greater thermostability and were active over a broader $Mg^{2+}$-range than the corresponding holoenzyme. Also, the deletion of the 5' to 3' exonuclease domain while maintaining an active 3' to 5' exonuclease (proofreading) domain in Ultma™ DNA Polymerase (Perkin Elmer, Branchburg, N.J.) is reported to provide an increase in fidelity. (Sninsky, Gelfand and Erdman, Amplifications, Perkin Elmer, 1995). While each of the above described enzyme fragments produced a different but useful property, it is wholly unpredictable whether a fragment of a polymerase enzyme will have a particular property.

However, there exists a need in the art for new, thermostable DNA polymerase enzymes for use in new molecular biology applications. More particularly, there exists a need for thermostable DNA polymerase enzymes having high purity, high DNA polymerase specific activity, high reverse transcriptase activity, low levels of exonuclease activity, and possessing high fidelity (low mutation frequencies) and high processivity.

An object of the present invention is to provide a polymerase enzyme preparation of greater purity, quantity, and processivity than has heretofore been possible. A further object is to eliminate the need and expense of culturing of large volumes of thermophilic bacteria at high temperatures that is associated with preparing native thermostable polymerase enzyme preparations. Yet another object is to provide a recombinant polymerase possessing 3'–5' exonuclease (proofreading) activity and higher reverse transcriptase activity as compared to the currently available enzymes (Bca polymerase, PanVera, Madison).

SUMMARY OF THE INVENTION

The present invention has multiple aspects. In its simplest form, the present invention is directed to a thermostable and enzymatically active recombinant fragment of a bacterial polymerase enzyme (*Bacillus stearothermophilus* DNA polymerase I) wherein the desirable DNA polymerase activity and 3'–5' exonuclease activity of the holoenzyme have been retained or enhanced and the undesirable 5'–3' exonuclease activity of the holoenzyme has been substantially removed. This recombinant polypeptide fragment, which is referred to herein as "rBst exo-," has a molecular weight of about 66,000 daltons and corresponds to amino acid residues 274–876 of SEQ ID NO: 2. Unexpectedly, it has been discovered that rBst exo- has significant reverse transcriptional activity i.e., a R.T. to polymerase ratio that is greater than 1.

The other aspects of the present invention are directed to the various intermediates that are used in preparation of this recombinant polypeptide fragment. More specifically, this invention is also directed to isolated and purified polynucleotides (e.g., cDNA, DNA sequences, complementary sequences and RNA transcripts thereof) encoding a thermostable polypeptide fragment of the DNA polymerase I enzyme of *Bacillus stearothermophilus* having DNA polymerase activity. Preferred DNA include: the isolated *Bacillus stearothermophilus* strain 10 DNA pol I gene comprising nucleotides described in FIG. 2a; nucleotide 316–2943 of SEQ ID NO: 1 (exclusive of the stop codon) or nucleotides 316–2946 of SEQ ID NO: 1 (inclusive of the stop codon) and; a portion of the insert of plasmid pPEK 5 (ATCC Accession No.#), said portion encoding a thermostable polypeptide having DNA polymerase activity. Also within the scope of this invention is rBst pol I (SEQ ID NO: 2) which is encoded by nucleotides 316–2946 of SEQ ID NO: 1 (inclusive of the stop codon). Additional DNA molecules within the scope of this invention are an isolated DNA or a cDNA having nucleotides 1135–2943 or 1135–2946 of (SEQ ID NO: 1) encoding the Bst exo- fragment (without and with the stop codon, respectively).

The present invention is also directed to a plasmid encompassing the above mentioned DNA molecules, e.g., pPEK 5 and pPRB5, and to a host cell, such as a prokaryotic or eukaryotic host cell that has been stably transformed with DNA vectors, or plasmids of the invention. Another aspect of the invention is directed to such transformed host cells that are capable of expressing a thermostable polypeptide encoded by the DNA of the present invention, the peptide having DNA polymerase activity.

In another aspect, this invention provides a purified thermostable polypeptide having DNA polymerase activity. Preferred peptides include a *Bacillus stearothermophilus* exo- DNA polymerase I fragment, which is substantially free of 5'–3' endonuclease activity or other *Bacillus stearothermophilus* proteins with 3'–5' exonuclease activity and substantially free of reduced 5'–3' exonuclease activity as compared to the holoenzyme.

In another aspect, this invention provides methods for purifying a thermostable polypeptide having DNA polymerase activity including the steps of transforming a host cell with a DNA of the present invention to create a transformed host cell; cultivating the transformed host cell under conditions that promote expression of a thermostable polypeptide encoded by the DNA, the polypeptide having DNA polymerase activity; and purifying the thermostable polypeptide. In the preferred method, commercially available chromatography columns are used to purify the expressed polypeptide.

In another aspect, this invention provides methods of using the DNA constructs of the invention to produce a recombinant thermostable polypeptide having DNA polymerase activity, 3'–5' exonuclease activity and being free of 5'–3' exonuclease activity. One such method involves using a DNA encoding a DNA polymerase enzyme to generate an active fragment of the DNA polymerase enzyme, including the steps of: deleting a portion of the DNA to create a modified DNA via restriction endonuclease cleavage; expressing the modified DNA to produce a DNA polymerase enzyme fragment; assaying the DNA polymerase enzyme fragment for DNA polymerase activity and selecting a DNA polymerase enzyme fragment having DNA polymerase activity wherein the DNA is selected from among the DNA described herein.

In another aspect, this invention provides methods for using the proteins of the invention in biological applications, such as in DNA sequencing, cDNA preparation, Strand Displacement Amplification and other applications or processes that would be apparent to those skilled in the art.

BRIEF DESCRIPIION OF THE DRAWINGS

FIG. 1 graphically depict the cloning strategy for the DNA encoding the exo- fragment of *B. stearothermophilus* DNA polymerase I. The abbreviations used are: D: Dra I; H: Hpa I; N: Nco I; Pr: Promoter; Sa: Sal I. Jagged lines (//////////) represent vector DNA; dark shaded rectangles depict the Bst exo- fragment DNA sequences and light shaded rectangles depict the 5'–3' exonuclease domain gene sequences. The graphical depictions are not drawn to scale, and not all available restriction sites are shown in all steps.

FIGS. 2a and 2b depict DNA and amino acid sequences for compositions of the present invention. FIG. 2a depicts the DNA sequence for the Bst DNA pol I coding sequence and for 5' and 3' untranslated sequences. Start codons for the holoenzyme and the exo- fragment are indicated by indentations and bold type. The sequence of the 757–830 probe fragment is underlined. The stop codon (TAA) is indicated by bold type. FIG. 2b depicts the deduced amino acid sequence for the Bst DNA pol I coding region. The bold typed amino acid (M) is the first amino acid believed to be translated during translation of plasmid pPEK 5, encoding the Bst exo- fragment. An asterisk (*) indicates the stop codon TAG.

Figure 5B:
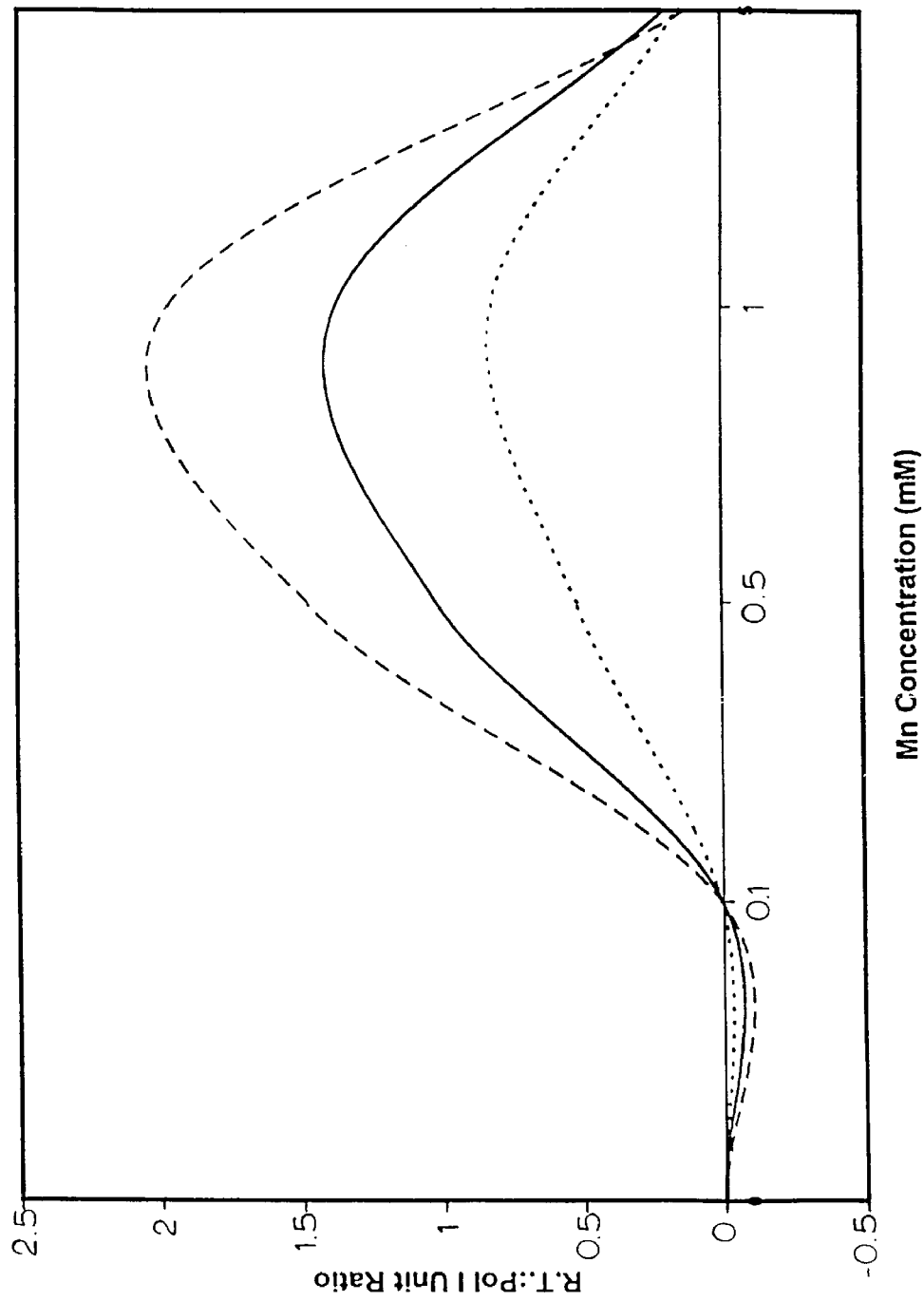

FIGS. 5a and 5b comparatively depict the various activities of the enzyme of the present invention as a function of $Mn^{++}$ concentration. FIG. 5a depicts the relative DNA polymerase enzymatic activity, at different concentrations of $MnCl_2$, of native *Bacillus stearothermophilus* exo- (nBst exo-: solid line); recombinant *Bacillus stearothermophilus* exo- (rBst exo-: dashed line); and recombinant *Bacillus caldotenax* exo- fragment (rBca exo-: dotted line, PanVera, Madison, Wis.).

FIG. 5b depicts the relative reverse transcriptase enzymatic activity at different concentrations of $MnCl_2$, of native *Bacillus stearothermophilus* exo- (nBst exo-: solid line); recombinant *Bacillus stearothermophilus* exo- (rBst exo-: dashed line); and recombinant *Bacillus caldotenax* exo- fragment (rBca exo-: dotted line, PanVera, Madison, Wis.).

Figure 6:
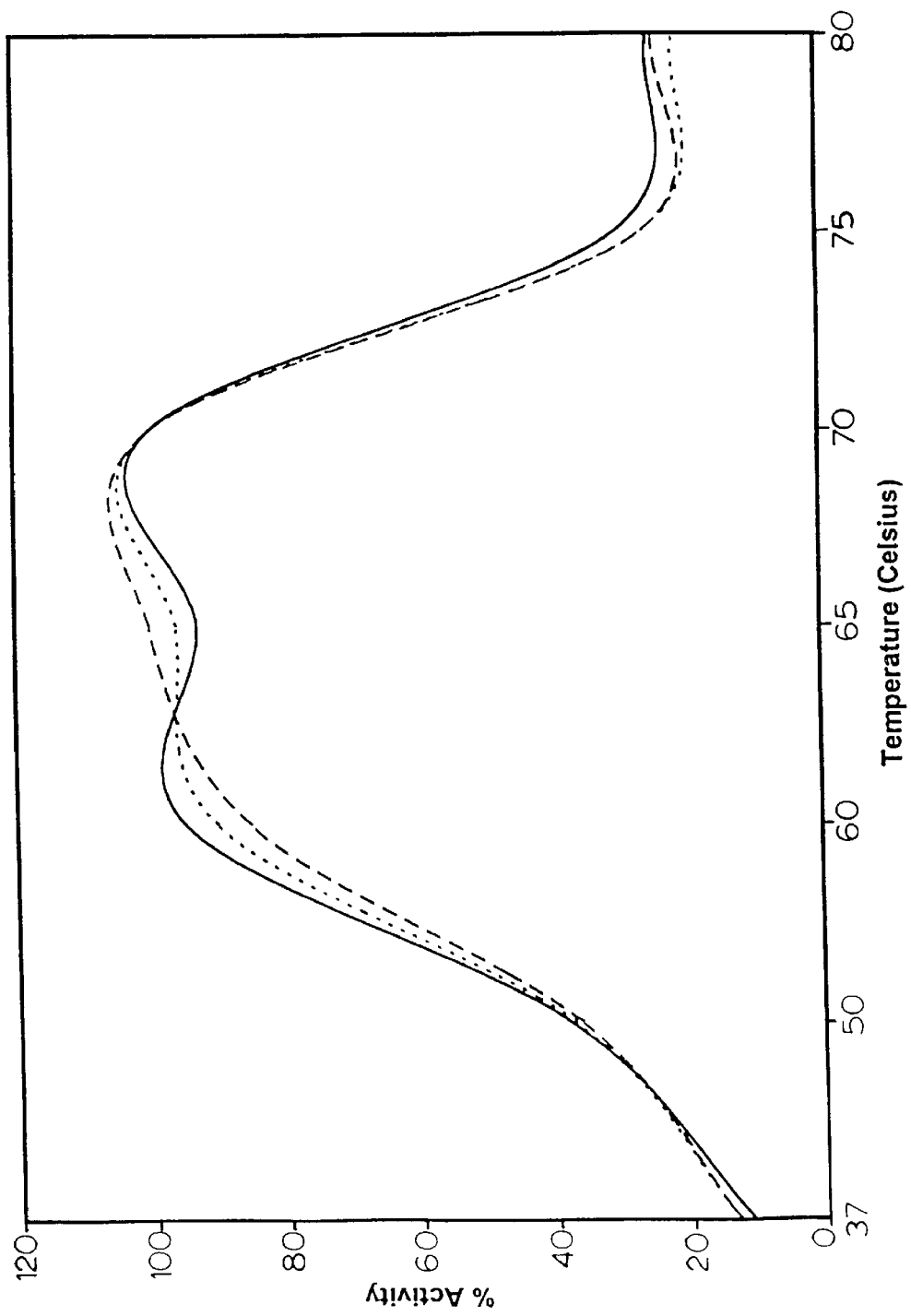

FIG. 6 depicts the relative DNA polymerase enzymatic activity, at different temperatures, of native *Bacillus stearothermophilus* exo- (nBst exo-: solid line); recombinant *Bacillus stearothermophilus* exo- (rBst exo-: dashed line); and recombinant *Bacillus caldotenax* exo- fragment (rBca exo-: dotted line, PanVera, Madison, Wis.).

Figure 7:

FIG. 7 photographically depicts a portion of an autoradiograph of reverse transcriptase products from poly rA:dT or mRNA targets using native *Bacillus stearothermophilus* exo- fragment (nBst exo-), recombinant *Bacillus stearothermophilus* exo- fragment (rBst exo-), and recombinant *Bacillus caldotenax* exo- fragment (rBca exo-). In FIG. 7, Lanes 1–6 contain the following: Lane 1, nBst exo- of mRNA; Lane 2, rBst exo- of mRNA; Lane 3, rBca exo- of mRNA; Lane 4, 1kb DNA Ladder; Lane 5, nBst exo- of poly rA:dT; Lane 6, rBst exo- of poly rA:dT; Lane 7, rBca exo- of poly rA:dT.

Figure 8:
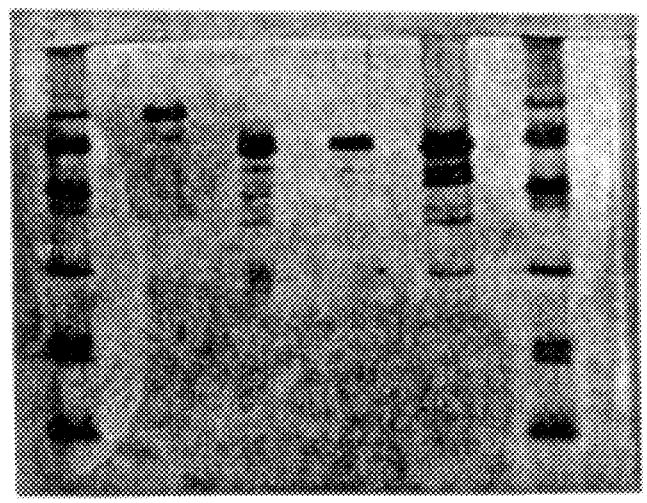

FIG. 8 photographically depicts the purity of purified native *Bacillus stearothermophilus* holoenzyme (nBst holo), native *Bacillus stearothermophilus* exo- fragment (nBst exo-), recombinant *Bacillus stearothermophilus* exo- fragment (rBst exo-), and commercially available recombinant *Bacillus caldotenax* exo- fragment (rBca exo-, PanVera, Madison, Wis.) on a 20.0% SDS-PAGE gel stained with silver. In FIG. 8, Lanes 1–6 contain the following polypeptides: Lane 1, Low Molecular Weight Markers; Lane 2, nBst holo; Lane 3, nBst exo-; Lane 4, rBst exo-; Lane 5, rBca exo-; and Lane 6, Low Molecular Weight Markers.

Figure 9A:
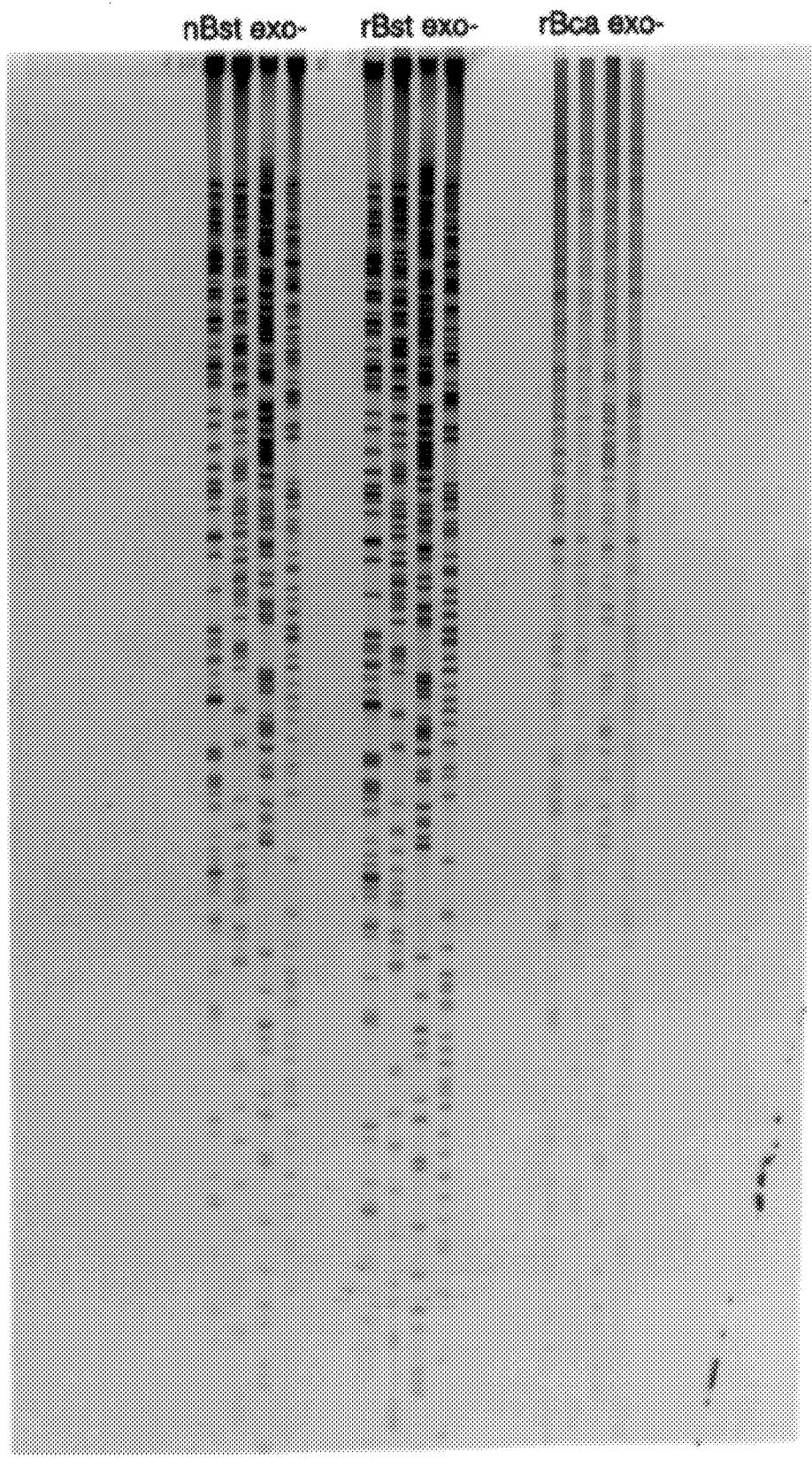
Figure 9B:
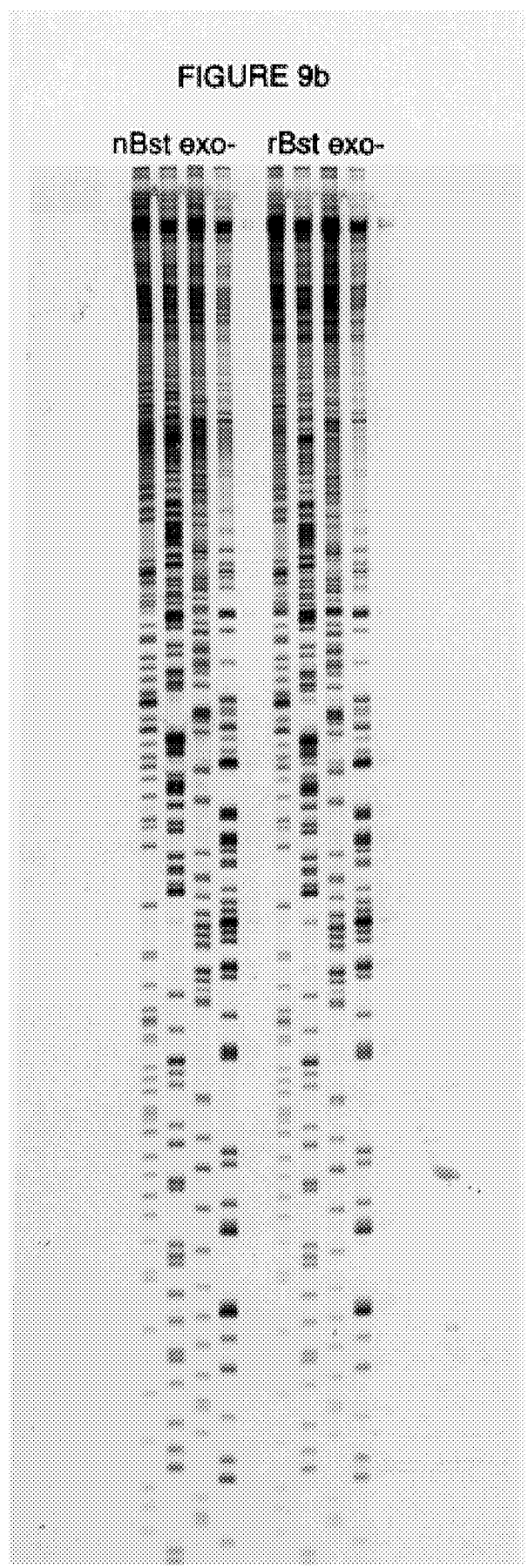

FIGS. 9a and 9b photographically depict portions of autoradiographs of sequencing gels showing DNA sequence obtained with the indicated polymerases. Abbreviations; native *Bacillus stearothermophilus* exo- fragment (nBst exo-); recombinant *Bacillus stearothermophilus* exo- fragment (rBst exo-); recombinant *Bacillus caldotenax* exo- fragment (rBca exo-).

Figure 10:
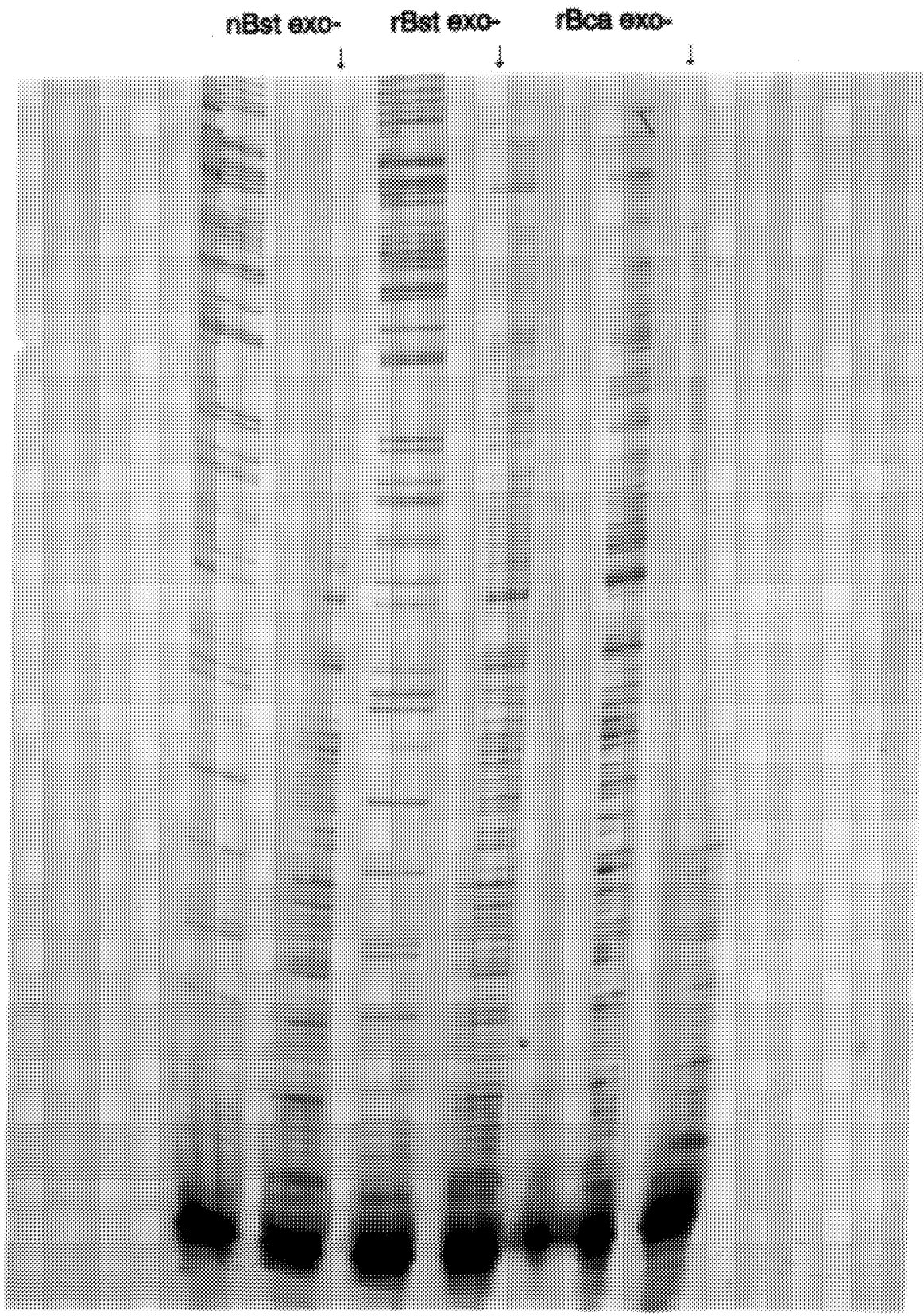

FIG. 10 photographically depicts portions of autoradiographs of sequencing gels showing processivity differences obtained with the indicated polymerases. Abbreviations; native *Bacillus stearothermophilus* exo- fragment (nBst exo-); recombinant *Bacillus stearothermophilus* exo- fragment (rBst exo-); recombinant *Bacillus caldotenax* exo- fragment (rBca exo-).

FIG. 11 photographically depicts a portion of an autoradiograph of thermophilic SDA products with recombinant *Bacillus stearothermophilus* exo- fragment (rBst exo-).

DETAILED DESCRIPTION OF THE INVENTION

In its first aspect, the present invention is directed to an isolated and purified DNA (nucleotides 316–2946 of SEQ ID NO: 1) encoding a biologically active, thermostable, full length DNA polymerase I enzyme of *Bacillus stearothermophilus*, ("Bst pol I"). By the phrase "thermostable" as used herein is meant an enzyme that exhibits thermal stability at 65°–80° C., preferably 65°–70° C. The present invention is also directed to a cDNA having nucleotides 316–2943 (exclusive of the stop codon) of SEQ ID NO: 1 or a cDNA having nucleotides 316–2946 (inclusive of the stop codon) of SEQ ID NO: 1, which enable the Bst pol I enzyme.

In another aspect, the invention is directed to a DNA (nucleotides 1135–2946 of SEQ ID NO: 1) encoding an approximately 66,000 dalton DNA polymerase that lacks 273 amino acids from the N-terminus of the approximately 96,000 dalton *B. stearothermophilus* DNA polymerase I (SEQ ID NO: 2), and to the protein encoded thereby which has been designated the *B. stearothermophilus* DNA polymerase I exo- fragment (i.e., amino acid residues 274–876 of SEQ ID NO: 2). The enzyme fragments are useful in DNA sequencing, cDNA preparations, thermophilic Strand Displacement Amplification and other molecular biology applications.

As a first step in the generation of the DNA and polypeptides of the present invention, native *B. stearothermophilus* DNA polymerase I was purified and isolated from *B. stearothermophilus* strain 10 cells (this strain was received from Bruce Roe, University of Okla.) and amino acid sequence information was determined for this 90–100 kilodalton (kD) native holoenzyme. (See Example 1.) Additionally, a *Bacillus stearothermophilus* genomic library was constructed in phage λ Dash II library and amplified. (See Example 2.)

Published amino acid sequence information from various Thermus species and *Bacillus caldotenax* DNA pol I genes (Uemori et al., *J. Biochem.* 113: 401–410 (1993) was used to create a degenerate set of synthetic DNA primers of which primers 757 (SEQ. ID NO: 4) and 830 (SEQ. ID NO: 5) were found useful for isolating a portion of the *Bacillus stearothermophilus* DNA polymerase I gene. Also, N-terminal amino acid sequence information of native Bst DNA polymerase I was determined (see Example 1) and used to create a synthetic primer, BCA (SEQ. ID NO: 3), to identify the 5' end of the *Bacillus stearothermophilus* DNA polymerase I gene (see Example 3). The 757 primer (SEQ. ID NO: 4) was synthesized to have a sequence which binds to the top strand of the *B. stearothermophilus* strain 10 DNA pol I gene. The 830 primer (SEQ. ID NO: 5) was synthesized to have a sequence that binds to the 3'-end of the *B. stearothermophilus* gene on the opposite strand. A DNA amplification reaction was performed with primer 757 (SEQ. ID NO: 4), primer 830 (SEQ. ID NO: 5), and *B. stearothermophilus* strain 10 genomic DNA. The amplification reaction yielded a single amplification product, designated the "757–830 fragment." This fragment was cloned into pTZ18U vector, amplified in *E. coli*, and sequenced.

As explained in detail in Example 4, the 757–830 fragment (obtained by the procedures outlined in Example 3) was further amplified and used to generate probes via thermal cycle labeling (TCL). The probes were used to isolate the *Bacillus stearothermophilus* DNA pol I gene from the *B. stearothermophilus* genomic library that had been constructed (See Example 2). The amplified *B. stearotheophilus* genomic library was plated on 2XTY plates and grown until plaques formed. Duplicate plaque lifts were obtained from each plate onto Hybond N filters, and these filters were then screened using the above described TCL probes using hybridization methods well known in the art. Positive plaques were selected, purified by dilution and re-screened with the 757 (SEQ ID NO: 4), 830 (SEQ ID NO: 5), and BCA (SEQ ID NO: 3) probes, and then further characterized. In particular, two clones with inserts of 14–16 kb, which were designated λ411 and λ511, were chosen for further analyses.

Figure 1:
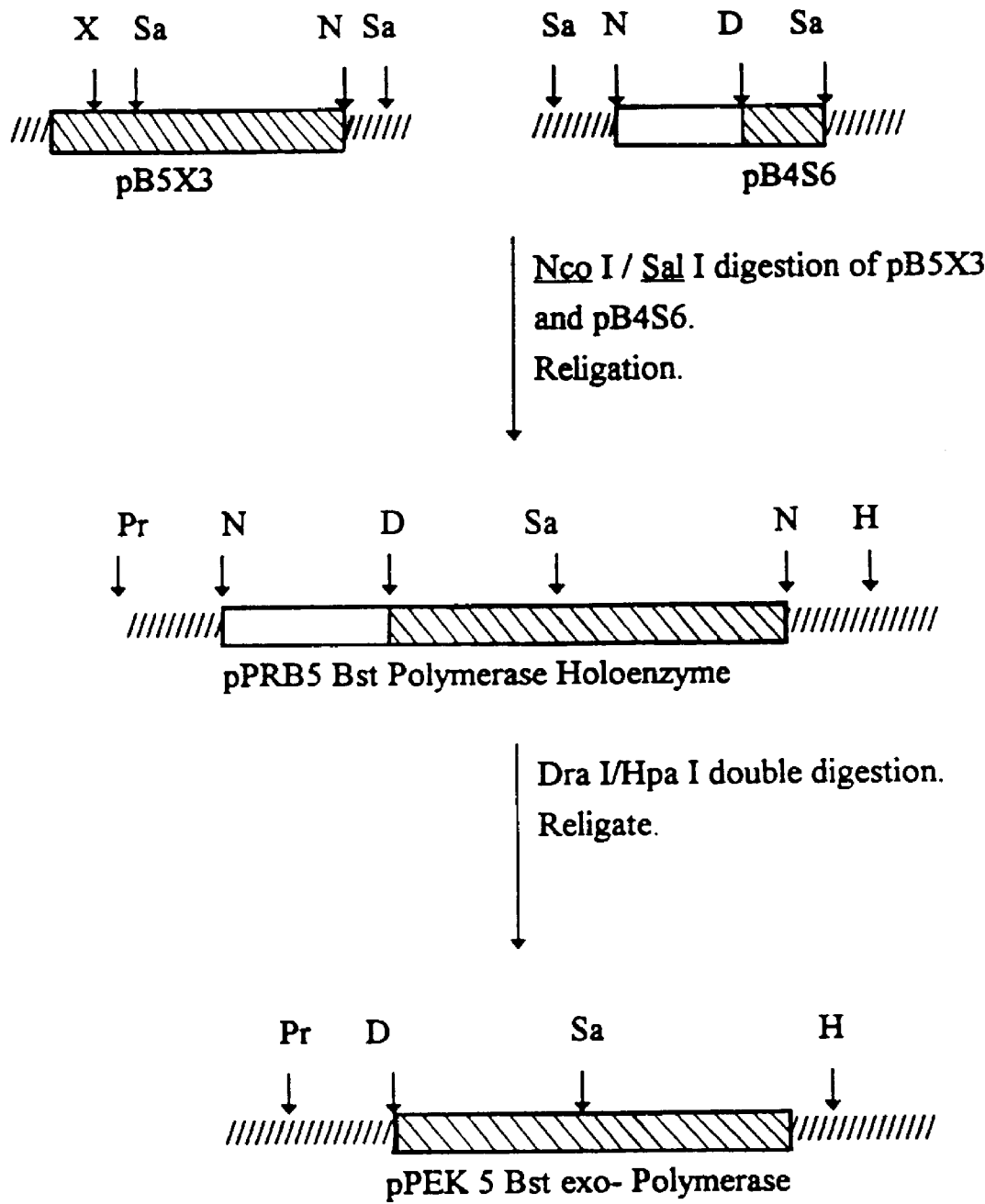

Clones λ411 and λ511 were used as a starting point from which the complete *B. stearothermophilus* DNA pol I gene was assembled and sequenced. As explained in detail in Example 5 and with reference to FIG. 1, restriction mapping, subcloning, and partial sequencing led to the determination that a subclone of λ511 designated pB5X3 contained about ½ of the Bst DNA pol I gene (3' end), whereas a subclone from λ411 designated pB4S6 contained the remaining 5' portion of the gene that overlapped the coding sequence contained in clone pB5X3.

A primer walking procedure was used to obtain the complete sequence of the gene. Specifically, primers homologous or complimentary to the ends of previously determined sequences were synthesized and used in additional sequencing reactions. By repeating this process, the entire length of the gene was sequentially sequenced.

The foregoing results demonstrate that an aspect of the invention is directed to a purified and isolated DNA encoding a thermostable polypeptide having DNA polymerase activity, the DNA comprising nucleotides described in FIG. 2a. This DNA may be operatively linked to other DNA, such as expression vectors known in the art. The invention is also directed to a vector having at least one insert consisting essentially of nucleotides described in FIG. 2a, the nucleotides encoding a thermostable polypeptide having DNA polymerase activity.

With the gene sequence established, the deduced amino acid sequences of the *B. stearothermophilus* DNA pol I gene were aligned and compared to the deduced amino acid sequences of the purported *B. caldotenax* DNA pol I gene (Uemori et al., *J. Biochem.* 113: 401–410 (1993). The following substitutions or deletions and their location were found in the rBst DNA pol I amino acid sequence when compared to the rBca DNA pol I sequence: Met $_{128}$, Trp $_{164}$, Trp $_{550}$, deletion $_{576}$.

To produce the recombinant *B. stearothermophilus* exo-DNA pol I protein of the present invention, a full-length *B. stearothermophilus* DNA pol I gene clone was constructed and expressed in *E. coli*. As detailed in Example 6 and FIG. 1, plasmids pB5X3 and pB4S6 were further restriction mapped and subsequently subcloned to generate plasmid pPRB5, containing a 3.5 kb insert containing the entire Bst DNA pol I gene along with 5' and 3' non-coding regions. A Dra I, Hpa I restriction fragment isolated from pPRB5 was ligated to a similar vector to generate the 5' deleted exo-fragment designated pPEK5

*E. coli* DH5αF' were transformed with plasmid pPEK5 and grown in a fermentor to recombinantly produce *B. stearothermophilus* exo- fragment. As detailed in Example 6, this recombinant protein was purified from the lysed *E. coli* with a method that included a heat denaturation of *E. coli* proteins, Mono Q and Mono S chromatography. The calculated DNA polymerase specific activity of *B. stearothermophilus* DNA exo- fragment isolated by this procedure was determined to be approximately 150,000 U/mg protein.

The foregoing description of methods and recombinant cells demonstrates that the present invention is directed to more than DNA and polypeptides. Another important aspect of the invention is directed to a host cell transformed with a DNA, vector, or plasmid of the present invention, including those specifically mentioned above. Preferably, the host cell transformed with the DNA is capable of expressing a thermostable polypeptide encoded by the DNA, wherein the polypeptide has DNA polymerase activity. By host cell is meant both prokaryotic host cells, including *E. coli* cells, and eukaryotic host cells.

In addition to being directed to DNA transformed cells, and polypeptides, the present invention is directed to various methods for using DNA and polypeptides. For example, the purification protocols for rBst exo- fragments demonstrate that another aspect of the invention relates to methods of purifying a thermostable polypeptide having DNA polymerase activity. One such method includes the steps of expressing the thermostable polypeptide in a host cell, the polypeptide having an amino acid sequence encoded by a DNA of the present invention; lysing the cell to create a suspension containing the thermostable polypeptide and host cell proteins and cell debris. Preferably, such a method further includes the steps of heating the suspension to denature the host cell proteins; and centrifuging the suspension to remove the cell debris and denatured host cell proteins. Further purification is achieved by Mono Q and Mono S chromatography, respectively.

As detailed in Example 9 and summarized in TABLE 3A, a number of experiments were conducted to characterize contaminating (non-polymerase related) exonuclease activities of purified *B. stearothermophilus* and *B. caldotenax* DNA pol I exo- fragments. The 5'–3' exonuclease and endonuclease activity assayed was either very low or undetectable. However, the relatively higher release of labelled substrate, which is evident in the 3'–5' exonuclease assays of nBst exo- and rBst exo- fragments compared to that of rBca exo- fragment while maintaining a zero slope of %-release/ unit enzyme, indicates an inherent 3'–5' exonuclease (proofreading) activity in the purified Bst exo- fragment enzyme.

Figure 3:
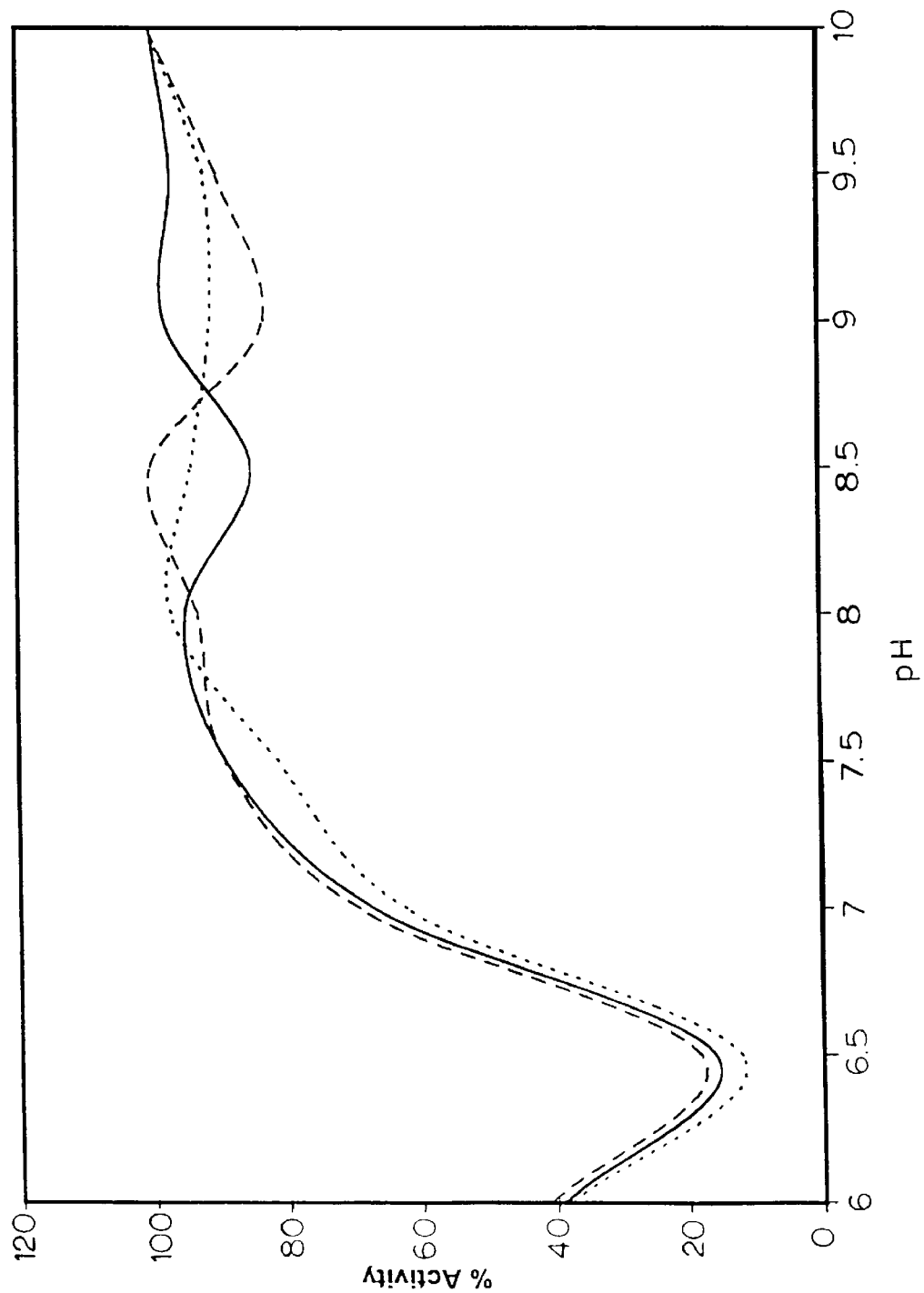
FIG. 3 depicts the relative DNA polymerase enzymatic activity, at different buffered pH levels, of native *Bacillus stearothermophilus* exo- (nbst exo-: solid line); recombinant *Bacillus stearothermophilus* exo- (rBst exo-: dashed line); and recombinant *Bacillus caldotenax* exo- fragments (rBca exo-: dotted line, PanVera, Madison, Wis.).

As detailed in Example 8, a number of additional assays were performed to better characterize the recombinant Bst exo- fragment protein that had been purified and to compare these proteins to recombinant *Bacillus caldotenax* exo-fragment (rBca exo-, PanVera, Madison, Wis.). For example, the DNA polymerase activity of the nBst, rBst and rBca exo-fragment was analyzed at different pH values, and at different $MgCl_2$ and $MnCl_2$ concentrations. FIGS. 3 (pH optima); 4 ($MgCl_2$ optima); 5a and 5b ($MnCl_2$ optima) and 6 (temperature optima) summarize the results of some of these assays. The optima for the recombinant Bst and Bca exo-fragments are summarized in TABLE 1.

TABLE 1

Optima for rBst exo- and rBca exo- fragments

|  | rBst exo- | rBca exo- |
| --- | --- | --- |
| pH | 7.5–10.0 | 7.5–10.0 |
| $MgCl_2$ [mM] | 1.0 | 1.0 |
| $MnCl_2$ [mM] | 0.5 | 0.5 |
| Temperature | 70° C. | 70° C. |

To assay for thermostability, the enzymes were incubated for 10 minutes at different temperatures to define the temperature optimum. The highest activity (over 90%) was found at 70° C. for nBst exo-, rBst exo-, and rBca exo-fragments with (approx. 20% remaining after 10 minutes at 80° C. for all three.

Reverse transcriptase (RT) (RNA dependant DNA polymerase) activity was detected in all three samples at 50° C., at a 1.0 mM $MnCl_2$ optimum concentration. Both the native and recombinant Bst exo- fragments yielded an RNA dependant DNA polymerase to DNA dependant DNA polymerase unit ratio equal to about 1.4 and 2.0, respectively, while the rBca fragment yielded a ratio equal to or less than 0.8. (FIGURE 5b).

The purified rBst exo- fragment was found to possess inherent 3'–5' exonuclease (proofreading) activity and no detectable 5'–3' exonuclease activities. The preparation was more than 90% pure as judged by 20% SDS-PAGE (FIG. 8). The apparent molecular weight of 65 kD as judged by SDS-PAGE compares well with the calculated molecular weight of approximately 65 kD. The rBst exo- preparation was found to be free of detectable double- and single-stranded nucleases and endonuclease contamination activities. The isoelectric point was determined to be 5.6.

The performances of nBst exo-, rBst exo-, and rBca fragments were tested in ssDNA sequencing (Example 9). The enzymes were useful in sequencing reactions utilizing internal labeling with [$\alpha^{33}$P]-dATP. In all the reactions tested, the exo- fragments provided readable DNA sequence information of more than 150 nucleotides. However, a stronger signal was evident with the native and recombinant Bst exo- fragments. Furthermore, the nBst and rBst exo- fragments were tested in dsDNA sequencing with results comparable to those seen with ssDNA target (Example 11B).

The following examples are intended to describe various aspects of the invention in greater detail. More particularly, in Example 1, the purification and N-terminal amino acid sequencing of native *Bacillus stearothermophilus* DNA polymerase I is described. In Example 2, the construction and amplification of a *Bacillus stearothermophilus* genomic DNA library is described. In Example 3, the cloning and sequencing of a *Bacillus stearothermophilus* DNA polymerase I gene-specific probe fragment is described. Example 4 details the preparation of gene-specific probes and screening of the *Bacillus stearothermophilus* genomic library for clones containing the *B. stearothermophilus* DNA pol I gene. Example 5 details the sequencing of the *B. stearothermophilus* DNA polymerase I gene by primer walking. Example 6 details the cloning of the *B. stearothermophilus* holoenzyme and the cloning and expression of the exo- fragment of *B. stearothermophilus* DNA polymerase I.

In Example 7–13, the Applicants compared the activities of the rBst exo- enzyme of the present invention to native Bst exo- and the prior art enzyme rBca exo- (PanVera, Madison, Wis.). In Example 7, the characterization of recombinant *B. stearothermophilus* exo- DNA polymerase I exonuclease activities is detailed. TABLE 3A, which summarizes the results of Example 7, reflects that only the enzyme of the present invention (rBst exo-) is free from contamination with 3'–5' exonuclease activity, 5'–3' exonuclease activity, ssDNAse activity, dsDNAse activity and endonuclease activity. In contrast, nBst exo- exhibited 0.06% release/unit of 5'–3' exonuclease activity, and rBca exo- exhibited 0.3% release/unit of enzyme of 5'–3' exonuclease activity and 0.05% release/unit of enzyme of dsDNAse activity.

Figure 4:
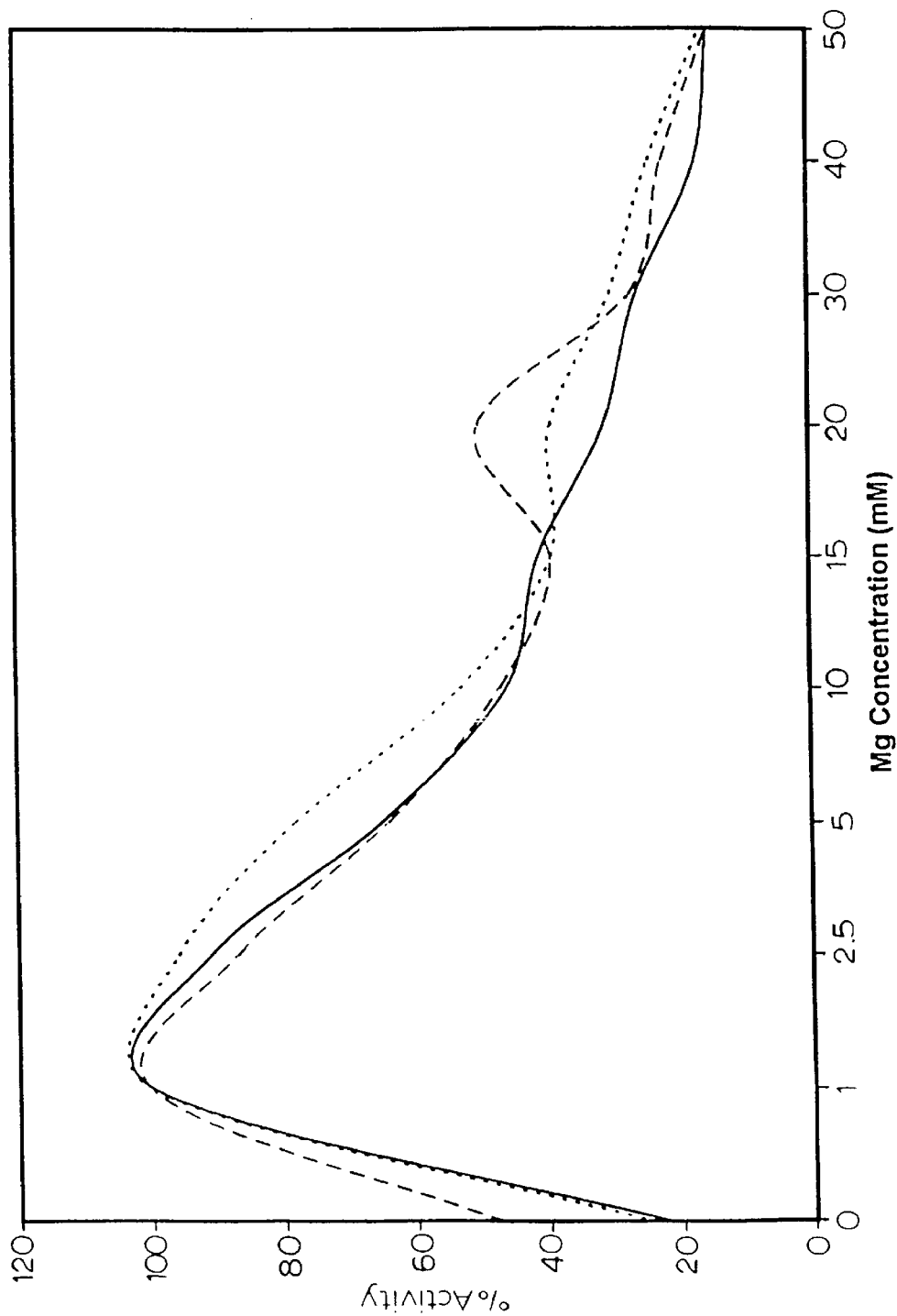
FIG. 4 depicts the relative DNA polymerase enzymatic activity, at different concentrations of $MgCl_2$, of native *Bacillus stearothermophilus* exo- (nBst exo-: solid line); recombinant *Bacillus stearothermophilus* exo- (rBst exo-: dashed line); and recombinant *Bacillus caldotenax* exo- fragment (rBca exo-: dotted line, PanVera, Madison, Wis.).

In Example 8, the effect of $MgCl_2$, $MnCl_2$, pH, and temperature on the activity of the native, recombinant *B. stearothermophilus* and recombinant *B. caldotenax* exo- DNA polymerases was compared. TABLE 4 in Example 8 reports that the pI for nBst exo-, rBst exo- and rBca exo- were determinable 5.4, 5.6 and 5.3, respectively. The optimal polymerase activity for each of these three enzymes was determined to be 1.0 mM $MgCl_2$ (See FIG. 4). In contrast, the optimal activity for the nBst exo-, rBst exo- and rBca exo- fragments was observed to be at 0.5 mM $MnCl_2$ (FIG. 5A). The temperature optima for all three enzymes, as depicted in FIG. 6, is 70° C., dropping precipitously to about 20% activity remaining at 80° C.

In Example 9, we demonstrated the utility of recombinant exo- fragment in reverse transcriptase (RT) procedures. Example 9 reflects that the ratio of reverse transcriptase (RT) units determined at the optimal of about 1.0 mM $MnCl_2$ concentration to polymerase I (pol I) units vary significantly between the three enzymes (See FIG. 5b). In particular, the ratio of RT:pol I obtained from the rBca exo- was 0.8 in contrast to about 1.4 and 2.0 for the nBst exo- and rBst exo- fragments, respectively. A ratio of RT:pol I that is greater than 1 is unexpected, and 2 or greater is very unexpected. It is also within the scope of the present invention that the Bst exo- fragment has an RT/pol I ratio of about 1 to 3, preferably 1.5–2.5.

In Example 10, DNA sequencing with recombinant *B. stearothermophilus* DNA polymerases was performed. Example 10 reflects that the precipitable cDNA obtained when using Poly rA:dT$_{50}$ as template was greatest with rBst exo- at 2941 cpm's followed by nBst exo- at 2421 cpm's and rBca exo- at 2001 cpm's. Alternatively, the use of mRNA as template resulted in 837,037 cpm, 691,545 cpm and 430,418 cpm for nBst exo-, rBst exo- and rBca exo- enzymes respectively (See TABLE 6). Also, the cDNA was determined by autoradiograph to be superior in length and quantity when using nBst exo- or rBst exo- fragments versus the cDNA product obtained when using rBca exo- fragment enzyme.

Example 11 compared the processivity (i.e., the rate of DNA polymerization along a template) of rBst exo- fragment to native Bst exo- and rBca exo- fragment. In this assay, the enzyme with the greatest processivity of DNA polymerase activity would produce the largest DNA molecules which would move slowly and stain darkly on electrophoresis relative to smaller DNA molecules. When the polymerase products of the three polymerases were placed on a 6% polyacrylamide sequencing gel, and electrophoresed, the order of processivity in descending order was rBst exo->nBst exo->rBca exo-. Thus, the enzymes of the present invention, rBst exo- and nBst exo-, both demonstrated superior processivity over the prior art enzyme rBca exo-. (See FIG. 10). Further, FIG. 10 demonstrates the overall superior processivity of rBst exo- (as reflected by the dark and multiple lines at the top of the figure) to both nBst exo- and rBca exo-.

In Example 12, the rBst exo- fragment was successfully used in thermophilic Strand Displacement Amplification. Accordingly, it is within the scope of the present invention that the Applicants' enzyme, particularly rBst exo-, be used in a thermophilic Strand Displacement Assay.

Finally, Example 13 details the purification of Bst exo- fragment in accordance with one embodiment of Applicants' invention. These and other embodiments of the Applicants' invention would be obvious to those skilled in the art based upon the disclosure herein and the Examples that follow.

EXAMPLE 1

Purification of Native Bst DNA Pol I and Native Exo- Fragment and N-Terminal Amino Acid Sequencing of Native Bst DNA Pol I Native *B. stearothermophilus* DNA polymerase I was isolated from *B. stearothermophilus* strain 10 cells and used to generate amino acid sequence information as described below.

A.

*Bacillus stearothermophilus* strain 10 (obtained from Bruce Roe University of Oklahoma) was cultured as follows: an isolated colony from an LB plate grown overnight at 55° C. was used to inoculate 100 ml culture medium (0.1 g nitrilotriacetic acid, 3 g NZ Amine A, 3 g yeast extract, 5 g succinic acid [free acid], 0.001 g riboflavin, 0.522 g $K_2HPO_4$, 0.480 g $MgSO_4$, 0.020 g NaCl, 2 ml Trace Metal Solution (0.5 ml $H_2SO_4$, 2.2 g $MnSO_4$, 0.5 g $ZnSO_4$, 0.5 g $H_3BO_3$, 0.016 g $CuSO_4$, 0.025 g $Na_2MoO_4$, 0.046 g cobalt nitrate per liter, adjusted to pH 8.0 with NaOH) and the culture was incubated overnight at 55° C. with shaking. In the morning, 10 ml of the overnight culture was used to inoculate 1000 ml of medium. This culture was grown for about 8 hours at 55° C. and then used as an inoculum for 170 liters of medium in a New Brunswick 250 liter fermentor equipped with a ML 4100 controller. The settings for a typical fermentation were 3 pounds back pressure, 60 liters per minutes (lpm) aeration, 100 rpm agitation, at 55° C. The fermentation was terminated when the cells reached a density of 2–3 O.D., as measured at 600 nm. The cells were cooled down to room temperature and harvested by centrifugation at 17,000 rpm in a CEPA type 61 continuous flow centrifuge with a flow rate of 2 lpm. The cell paste was stored at −70° C.

B. stearothermophilus strain 10 cells (500 g) were thawed in 3 volumes of lysis buffer (20 mM Tris-HCI, pH 7.5, 0.5 mM ethylenediaminetetraacetate (EDTA), 1 mM Dithiothreitol (DTT), 10 mM $MgCl_2$, 0.02% Brij 35) and homogenized. The suspension was then treated with 0.2 g/l of lysozyme (predissolved in lysis buffer) at 4° C. for 45 minutes. Cells were homogenized twice at 9000 psi in a Manton Gaulin homogenizer with the suspension chilled to approximately 10° C. between passes. The sample was mixed well and centrifuged at 13,500× g for 1 hour. A sample of the supernatant was titrated with a 10% polyethylenimine (PEI) solution to determine optimum PEI precipitation. The full scale PEI precipitation was centrifuged at 13,500 for 1 hour. The recovered supernatant was $AmSO_4$ precipitated at 70% saturation and allowed to stir at 4° C. for at least 60 minutes. After centrifugation at 9000 rpm for 60 minutes the pellets were resuspended in 300 ml of P-11 buffer (20 mM Kpi, pH 6.5, 1.0 mM DTT). The sample was dialyzed overnight at 4° C.

After clarification of the dialyzed sample by centrifugation at 9000 rpm for 10 minutes, the sample was loaded onto a 400 ml pre-equilibrated P-11 column (4.4×27 cm) at a flow rate of 2.5 ml/minutes The column was washed with 1 L of P-11 buffer. Elution of the enzyme was achieved by application of a 2800 ml linear gradient of P-11 buffer versus P-11 buffer at 300 mM KPi, pH 6.5. The fractions were assayed for Bst polymerase activity as described below and pooled. The P-11 pool was dialyzed for at least 3 hours versus 14 liters of Buffer B, (20 mM Tris-HCI, pH 7.5, 0.5 mM EDTA, 1.0 mM DTT, 10 mM $MgCl_2$, 0.02% Brij 35).

The dialyzed P-11 pool was harvested and adjusted to a conductivity of less than 2.5 milli-mhos with cold $H_2O$ and adjusted to a pH of 7.5 with 2N NaOH. The sample was applied to a 200 ml MBR Blue column (Cibacron Blue) and washed with 600 ml of Buffer B. The enzyme was eluted by application of a 2800 ml linear gradient of Buffer B versus Buffer B at 1.80M NaCl. The fractions were assayed for Bst polymerase activity as described below and pooled. This MBR Blue pool was dialyzed against 14 L of Buffer B for at least 3 hours.

The dialyzed MBR Blue pool was harvested and adjusted to a conductivity of less than 2.5 milli-mhos with cold $H_2O$ and a pH of 7.5 with 2N NaOH. The sample was applied to a 100 ml Heparin-Agarose column and washed with 200 ml of Buffer B. The enzyme was eluted by application of a 1500 ml linear gradient of Buffer B versus Buffer B at 0.75M NaCl. The fractions were assayed for Bst polymerase activity as described below and pooled. The Heparin-Agarose pool was dialyzed against 14 L of Buffer B for at least 3 hours.

The dialyzed Heparin-agarose pool was harvested and adjusted to a conductivity of less than 2.5 milli-mhos with cold $H_2O$ and a pH of 7.5 with 2N NaOH. The sample was filtered through a 0.8/0.2 μm unit and applied to a pre-packed Pharmacia 10×10 HP Q-Sepharose column. After a 100 ml wash with Buffer B, the enzyme was eluted with a linear 900 ml gradient of Buffer B versus Buffer B at 0.25M NaCl. The fractions were assayed for Bst polymerase activity as described below and pooled. The HP Q-Sepharose pool was used to isolate native Bst DNA pol I for N-terminal amino acid sequencing as described below.

An aliquot of the HP-Q Sepharose pool was digested with subtilisin (Karlsberg type, Sigma) to determine optimum digestion time to yield a 65 kD product as seen by 12.5% SDS-PAGE while retaining at least 80% activity. After treating the entire pool, the 65 kD fragment was purified from other fragments by application onto a pre-packed Pharmacia 5×5 Mono Q column. After a 10 ml wash with Buffer B, the enzyme was eluted with a 60 ml linear gradient of Buffer B versus Buffer B at 0.25M NaCl. The fractions were assayed for activity as described below and for purity by 12.5% SDS-PAGE before pooling. The pool was dialyzed against 2 L of final storage buffer (20 mM Kpi, pH 6.8, 1.0 mM DTT and 50% glycerol).

To quantify DNA polymerase activity, a DNA polymerase activity assay was performed using a modification of a protocol described by Kaledin et al., Biokhimiya 45: 644–651 (1980). Reactions were performed in a 50 μl reaction mixture of 50 mM Tris-HCI, pH 8.6 at 23° C.; 100 mM KCl; 10 mM $MgCl_2$; 1 mM DTT; 0.2 mM each dCTP, dGTP, dTTP, pH 7.0; 0.2 mM [$\alpha^{33}$P]dATP, pH 7.0,10 μCi/ml; 50 μg BSA; 15 μg activated DNA (Baril et al. Nucleic Acids Res. 8:2641–2653 (1977)); and 5 μl of diluted enzyme. Dilution Buffer consisted of: 50 mM Tris-HCI, pH 8.0 at 23° C., 1 mM DTT, 1 mM EDTA, 0.1% Brij-35 and 10% (v/v) glycerol. For control purposes, native Bst exo-DNA polymerase with known activity was diluted to 20, 40 and 80 units/ml. Two reactions were run without enzyme as negative controls for background subtraction.

A 45 μl reaction mixture, less enzyme, was prepared and the reaction was started by the addition of 5.0 μl of enzyme. After 10 minutes of incubation at 60° C., 40 μl was removed and added to 50 μl of yeast RNA co-precipitant (10 mg/ml in 0.1M sodium acetate, pH 5.0). One ml of 10.0% trichloracetic acid (TCA), 2.0% sodium pyrophophate was added and the samples were allowed to precipitate on ice for at least 10 minutes. The mixture was filtered on a glass fiber filter disc and washed first with 5% TCA/ 2% sodium pyrophosphate, and then with 100% Reagent grade ethanol (Mallinkrodt). The dried filter disc was counted in 5.0 ml of scintillation fluid.

One unit of activity is defined as the amount of enzyme required to incorporate 10 nmol of total nucleotide into acid insoluble form in 30 minutes at 60° C. in this standard activity assay.

The protein concentration was determined by Bradford Protein Assay (BioRad, Hercules, Calif.). The calculated DNA polymerase specific activity for the nBst exo- fragment was approximately 50,000 U/mg.

B.

To obtain amino acid sequence information from the isolated and purified native B. stearothermophilus DNA polymerase, about 50 μg of the native Bst DNA polymerase holoenzyme was separated on a preparative 7.5% SDS-polyacrylamide gel, blotted onto PVDF membrane and stained with amido black as described by Matsudaira, *J. Biol. Chem.* 262: 10035–10038 (1987). The major band at approximately 92 kD was excised and sequenced using an Applied Biosystems (Foster City, Calif.) 477A Protein Sequencer. The following sequence was found:

Met,Lys,Lys,Lys,Leu,Val,Leu,Ile,Asp,Gly,Ser,Ser,Val, Ala,Tyr,Arg.

This sequence has been determined to map at positions 1 to 16 in the deduced amino acid sequence of the Bst DNA pol I holoenzyme (SEQ ID NO: 2) as shown in FIG. 2b. As explained in Example 3, knowledge of this amino acid sequence information was used to isolate the *B. stearothermophilus* DNA polymerase I gene.

EXAMPLE 2

Construction and Amplification of a *Bacillus stearothermophilus* genomic DNA library A *Bacillus stearothermophilus* genomic library was constructed in phage λ Dash II and amplified in the following manner.

Genomic DNA from the *Bacillus stearothermophilus* strain 10, cultured overnight as described above, was isolated according to the procedure described by Ausubel et al., Current Protocols in Molecular Biology, Greene Publishing Associates and John Wiley & Sons, N.Y. (1990). In general, yields of genomic DNA between 100 and 900 μg were obtained from the cell pellet of about 1.5 ml of culture.

One microgram of *Bacillus stearothermophilus* strain 10 genomic DNA was digested with 1.0 unit of Sau 3A I in a total volume of 100 μl. At 0, 5, 10, 15, 20, 25, 30, 35, 40, 45 and 50 minutes, 5 μl samples were removed and the enzyme was inactivated at 70° C. for 10 minutes From each time point, aliquots were analyzed on a 1.2% agarose/TBE gel. The 45 minutes time point displayed the desired size distribution or 3 kb to 20 kb fragments. A scale-up digestion was performed using 20 μg of *Bacillus stearothermophilus* strain 10 genomic DNA, 20.0 units of Sau 3A I and a total volume of 250 μl.

Approximately 2600 pmoles of 5'-ends of Sau 3A I-digested *B. stearothermophilus* DNA were treated with 20 units of calf intestinal alkaline phosphatase for 30 minutes at 37° C., (CIP; Ausubel et al. (1990). The Sau 3A I digested, CIP treated *B. stearothermophilus* DNA was extracted with phenol/chloroform and chloroform, ethanol precipitated, pelleted, and washed in 70% ethanol. Two microliters of this DNA solution was visualized on a 1.2% agarose/TBE gel to check for amount and integrity. The pellet was stored at –20° C. This DNA is referred to as "CIP DNA".

The *B. stearothermophilus* library was constructed as described in the manufacturers instructions using the phage λ DASH II/Bam HI Cloning Kit (Stratagene, LaJolla, Calif.). The pME/Bam HI test insert (0.3 μg) was run in parallel as a control. The ligation mixture was incubated overnight at 4° C. One microliter of the ligation samples were run on a 1.2% agarose/TBE gel to check ligation efficiency.

The *B. stearothermophilus* DNA ligated to λ DASH II arms was packaged in vitro using the Gigapack II Gold Packaging Extract from Stratagene, according to the manufacturer's conditions. Control DNA provided by the manufacturer was also packaged.

Following the protocol provided by Stratagene with the Lambda DASH II/BamHi Vector Kit, host bacteria were prepared: VCS 257 for wild type phage, SRB and SRB(P2) for the *B. stearothermophilus* library and the control. VCS 257 was grown in NZY+maltose medium and SRB, and SRB(P2) were grown in NZY+maltose medium with 50 μg/ml kanamycin at 37° C. for 6 hours. After centrifugation of the cells at 2800×g for 10 minutes, the cells were resuspended with sterile 10 mM $MgSO_4$ to give an $A_{600\ nm}$ of 0.5.

One microliter of the following dilutions were added to 200 μl of SRB cells.

Two 1:10 serial dilutions were prepared from the control phage and the CIP Bst DNA library. Ten microliters of undiluted, 1:10, and 1:100 dilutions of phage were added to 200 μl of SRB cells. The cells were incubated with light shaking at 37° C. for 15 minutes and after the addition of top agar, the mixture was poured onto LB/M/M plates. (15 g agar, 10 g tryptone, 5 g yeast extract, 10 g NaCl, 2.64 g $MgSO_4$, 2 g maltose to 1000 ml with deionized $H_2O$, pH to 7.0 with 0.1N NaOH) The plates were incubated overnight at 37° C. After overnight incubation at 37° C., titer was determined by average plaque forming units per ml (pfu/ml).

The *B. stearothermophilus* library was amplified using techniques described by Ausubel et al., Current Protocols in Molecular Biology (1990). The primary and amplified libraries were titered on SRB cells. (TABLE 2). The amplified library was stored at 4° C.

TABLE 2

| | Titer plaque forming units/ml) | |
|---|---|---|
| Construct | Primary Library | Amplified Library |
| CIP BST DNA | $3.0 \times 10^5$ | $1.25 \times 10^9$ |
| pME/BamHI | $2.5 \times 10^6$ | Not determined |
| Control DNA | $1.19 \times 10^9$ | Not determined |

EXAMPLE 3

Cloning and Sequencing a Bst DNA Pol I Gene-Specific Probe Fragment

The DNA sequences from Thermus species and *Bacillus caldotenax* were used to design the synthesis of two primers for the amplification of a *B. stearothermophilus* DNA polymerase gene fragment: primer 757 (25 mer) (SEQ ID NO: 4) and primer 830 (23 mer) (SEQ ID NO: 5) (synthesized by Synthetic Genetics, San Diego, Calif.). Primer 757 corresponds to nucleotides 2584–2609 of SEQ ID NO: 1 of the *B. stearothermophilus* DNA polymerase coding sequence, top strand (i.e., to a portion of the DNA sequence that encodes a portion of the Bst DNA pol I protein that is homologous to Peptide 1). Primer 830 hybridizes to the 3'-end of the Bst DNA pol I gene at position 2794–2816 and has a sequence identical to the bottom strand.

The specificity of the primers 757 (SEQ ID NO: 4) and 830 (SEQ ID NO: 5) for *B. stearothermophilus* genomic DNA was demonstrated by screening Southern blot transfers of genomic DNA from *B. stearothermophilus, T. flavus, T. rubrum,* and *T. thermophilus*. Both the biotin-11 dUTP end labelled primers 757 (SEQ ID NO: 4) and 830 (SEQ ID NO: 5) hybridized strongly to *B. stearothermophilus* genomic DNA under high stringent conditions (52° C., 0.1×SSC, 1.0% SDS). Additionally, the end labelled primer 830 (SEQ ID NO: 5) detected blots of digested *B. stearothermophilus* genomic DNA. Specifically, Bst genomic DNA was digested with different restriction enzymes, such as Eco RI and Sau 3A I for 10, 15, 30 and 60 minutes. 500 ng/lane of restricted DNA was electrophoresed on a 0.7% agarose gel. A Southern transfer of this gel onto Hybond-N was prepared. The denatured DNA on the Southern blots was UV-cross-linked to the filter for 3.0 minutes. Duplicate blots were prehybridized in 2 ml of hybridization buffer (50% deionized formamide, 7% SDS, 120 mM Na phosphate, pH 7.2, 250 mM NaCl, 1 mM EDTA and 1 mM cetyldimethylethylammonium bromide and 20 μl of denatured salmon sperm DNA at 10 mg/ml) in a heat-sealed plastic bag at 52° C. for 1 hour. Approximately 250 ng of the end labelled probe was added per blot and incubated overnight at 50° C. The Southern blots with the labelled probe were incubated with low stringency buffer (1×SSC, 1.0% SDS) for 1 hour at 52° C., washed with high stringency buffer (0.1×SSC, 1.0% SDS) for 1 hour at 52° C., dried, and then detected by avidin-alkaline phosphatase conjugates.

An amplification reaction (100 μl) was performed containing 0.2 mM dNTPs, 1× Cetus AmpliTaq Reaction Buffer (10 mM Tris-HCl, pH 8.4, 500 mM KCl, 15 mM $MgCl_2$, 0.01% gelatin), 30 pmoles of each primer, 200 ng of Eco RI digested Bst genomic DNA, 5 units of AmpliTaq® DNA polymerase (Perkin Elmer No. N801-0060), and a 50 μl light mineral oil overlay. The amplification was performed in thirty cycles of 91° C. for 20 seconds, 55° C. for 20 seconds and 72° C. for 2 minutes.

Under these conditions, primer set 757–830 gave a single amplification product from Bst genomic DNA. The calculated length of 232 base pairs for the amplification product coincided with the observed mobility in 0.7% agarose/TBE gels. This fragment was ligated into pTZ18U as described by the Pharmacia Sure Clone Kit. Clones, which were sequenced as described in the Sequal DNA Sequencing Kit (CHIMERx, Madison, Wis.), were shown to have homology to *Bacillus caldotenax* DNA polymerase. Hence the 232 bp fragment was used to make probes as described in the ZEPTO™ labelling kit manual (CHIMERx, Madison, Wis.).

EXAMPLE 4

Preparation of Gene-Specific Probes and Screening of the *Bacillus stearothermophilus* Genomic Library for Clones Containing *B. stearothermophilus* DNA Pol I Gene The 757–830 fragment described in Example 3 was used to isolate the Bst DNA pol I gene from the Bst genomic library (See Example 2). Using the cloned 757–830 fragment as template and primers 757 (SEQ ID NO: 4) and 830 (SEQ ID NO: 5), the 757–830 fragment was first amplified by PCR as described above to obtain larger quantities of the fragment for use in preparing probes to screen the Bst genomic library. The amplified 757–830 fragment, migrating at about 240 bp, was cut out of a preparative 0.7% agarose TBE gel, eluted, phenol-chloroform extracted and ethanol precipitated. Approximately 1 μg of the 757–830 fragment was digested with Cvi JI* (CHIMERx, Madison, Wis.) to generate sequence specific primers for labelling as described in the ZEPTO™ labelling manual. Each set of duplicate plaque lifts or targets was screened using the 757–830 fragment labelled with [$^{33}$P]dCTP. Digestion with Cvi JI*, as well as this method of labeling, is described in a co-owned, copending U.S. patent application Ser. No. 08/217,459, filed Mar. 25, 1994, entitled "Methods and Materials for Restriction Endonuclease Applications," incorporated herein by reference in its entirety. The PCT counterpart of this application, filed Mar. 24, 1994, is PCT App. No. US94/03246.

The 757–830 intact fragment was labelled with [$^{33}$P]dCTP as described in the ZEPTO™ labeling manual; a total of $6\times10^7$ cpm of [$\alpha^{33}$P]dCTP at $1\times10^9$ cpm/μg was incorporated. For probes, $1-5\times10^6$ cpm of radio-labelled DNA was added to each plaque lift.

To screen the amplified *B. stearothermophilus* genomic library (Example 2), the phage library was plated on two plates each at $10^5$ plaque-forming units (pfu)/100 mm 2XTY plates. Duplicate plaque lifts on Hybond N from each plate were obtained and prepared for hybridization by methods well known in the art (Sambrook, Fritsch, and Maniatis, Molecular Cloning, A Laboratory Manual, 2nd ed., Cold Spring Harbor Press, Cold Spring Harbor, N.Y. (1989)). The DNA on the plaque lifts was UV-cross-linked to the Hybond N for 3 minutes and placed in a heat-sealed plastic bag for prehybridization as described above. $1-5\times10^8$ cpm of the [$\alpha^{33}$P]dCTP 757–830 TCL probe were added to the duplicate filters. The filters were incubated overnight at 52° C. and washed the next day with low and high stringency buffers as described above.

Four positive plaques (hybridizing with the labelled probes) out of $10^5$ pfu from the amplified CIP Bst DNA library were detected on the duplicate plaque lifts. These four stocks of phage designated λB211, λB411, λB511, and λB711 were grown to $5\times10^5$ pfu/2XTY plate, 5 plates per stock. The phages were eluted from the plates by a standard protocol (Sambrook et al. (1989)). The eluant was treated with 20 μg/ml DNAse and 50 μg/ml RNase A for 1 hr. at 37° C. and extracted with both phenol-chloroform and chloroform. The DNA was ethanol-precipitated, pelleted, washed with ethanol, resuspended in 1 ml of TE buffer (10 mM Tris pH 8.0, 1 mM EDTA) and purified as described in the Lambda DNA Purification Kit (CHIMERx, Madison, Wis.).

Phage DNA λB211 was restriction-digested with EcoRI, λB411 with Sal I, λB511 and λB711 with XbaI. After digestion, each phage DNA was separately ligated into pTZ18U (Mead et al., Protein Engineering 1: 67–74 (1986)) that had been similarly digested and dephosphorylated to minimize self-litigation. The plasmid derivatives of these clones were designated pB2, pB4S, pB5X and pB7X respectively.

After transformation, clones were verified by sequence homology to Bca sequence data and/or by hybridization with labelled 757 or 830 primers under the hybridization conditions described previously. This information confirmed that the clones contained authentic *B. stearothermophilus* strain 10 DNA polymerase gene sequence and their respective orientations.

EXAMPLE 5

Sequencing the *B. stearothermophilus* DNA Polymerase I Gene and cloning of the *B. stearothermophilus* DNA Polymerase I and exo-Fragment A primer walking sequencing strategy was employed to obtain the sequence of the Bst DNA pol I gene (Sambrook et al., Molecular Cloning. A Laboratory Manual. Cold Spring Harbor Press (1989)). To obtain sequence information from the clones by primer walking, primers homologous or complimentary to the ends of previously determined sequences were synthesized as described above and used in additional sequencing reactions (TABLE 2, Bseq1–25). By repeating this process, the entire length of the gene was sequentially sequenced.

Clones λ411 and λ511 were confirmed to include both the 5' and 3' Bst DNA pol I coding sequences as described in Example 4. Sequence analysis of these clones provided advantageous restriction endonuclease sites which were used to join the 5' and 3' sequences to obtain a complete Bst DNA pol I encoding insert. In particular, a shared singular Sal I site and an available Nco I site were used. An expression vector designated pPR was digested with BspH I for subsequent ligation to the complete Bst DNA pol I encoding insert. BspH I restricted sites can serve as compatible cohesive ends for ligation with Nco I restricted sites due to identical overhang termini. After transformation and confirmation of the Bst pol I insert, expression of the encoded Bst DNA pol I polypeptide was successfully achieved utilizing the temperature dependant pR operator/promoter region. Sequence information determined that a singular Dra I site located at the junction of the nucleotide sequence encoding the 5'–3' exonuclease domain and the 3'–5' proofreading domain. Therefore, restriction with this enzyme and subsequent religation yielded an intact exo-fragment in frame with the pR operator/promoter. After transformation and confirmation of the exo- fragment insert, expression of the encoded Bst exo- fragment polypeptide was successfully achieved.

The DNA sequence of the *B. stearothermophilus* DNA polymerase I gene, the exo- fragment and the flanking sequences (italicized) are given in FIG. 2a. Also, the translated deduced amino acid sequence is given in FIG. 2b for the holo and exo- fragments. The DNA sequence of 3317 b.p. (SEQ ID NO: 1) for the Bst DNA polymerase I gene has been determined, of which 2631 bases (i.e., nucleotides 316–2946 of (SEQ ID NO: 1)) are deduced to encode a nBst pol I polypeptide (SEQ ID NO: 2) of 877 amino acids (including the TAA stop codon), and of which nucleotides 1135–2946 encode the Bst exo- fragment (including the TAA stop codon).

EXAMPLE 6

Cloning and Expression of the exo- Fragment of *B. stearothermophilus* DNA Polymerase I Expression studies using plasmid pPEK 5, which contains the 3' two-thirds of the DNA polymerase I gene fused to the pR operator/promoter, was performed. As deduced from the DNA sequence, the putative first amino acid encoded by the insert of plasmid pPEK 5 corresponds to Met in FIG. 2b (bold type), i.e., residue 285 of SEQ ID NO: 2. It was hypothesized that the insert in pPEK 5 would encode a fragment of DNA polymerase I lacking the 5'–3' exonuclease domain (the Bst exo- fragment) due to the absence of the 5' one-third portion of this gene.

*E. coli* DH5αF' [pPEK 5] was grown in a 4 liter Erhlenmeyer flask in LB medium (Sambrook et al., Molecular Cloning, A Laboratory Manual, 2nd ed. (1989)) supplemented with 50 µg/ml ampicillin with vigorous aeration at 30° C. At O.D.$_{600\ nm}$=1.0, the culture was induced by transferring to a 42° C. incubator and allowed to grow an additional 2 hours. The culture was spun down in a Sharples centrifuge and stored frozen at −70° C.

One and one-quarter grams of *E. coli* [pPEK 5] were thawed in 10 ml of lysis buffer (20 mM Tris-HCl pH 8.0, 0.5 mM EDTA, 50 mM NaCl, 1 mM DTT, 0.02% Brij-35, 0.1 mg/ml lysozyme, and 1.0 mM PMSF). The cell suspension was allowed to stir at room temperature for 30 minutes. The lysate was heated to 65° C. for 15 minutes then cooled on ice for 5 minutes. After centrifugation at 12000 rpm for 30 minutes to remove cell debris and denatured proteins, the supernatant was filtered through a 0.8/0.2 µm filtration unit and applied to a prepacked Pharmacia 5×5 Mono Q column equilibrated in Buffer A: 20 mM Tris-HCl, pH 7.5, 1.0 mM DTT, 0.5 mM EDTA, 10 mM MgCl$_2$, and 0.02% Brij-35. After washing with 20 ml of Buffer A, the enzyme was eluted with a 90 ml linear gradient of Buffer A versus Buffer A at 0.4M NaCl. The 1 ml fractions were assayed for activity and pooled accordingly.

The Mono Q pool was diluted with Buffer A at pH 6.0 to reduce the conductivity to 5 milli-mhos and lower the pH to 6.0. The pool was then applied to a prepacked Pharmacia 5×5 Mono S column equilibrated in Buffer A at pH 6.0. After washing with 20 ml of equilibration buffer, the enzyme was eluted with a 90 ml linear gradient of Buffer A, pH 6.0 to Buffer A, pH 6.0 at 0.75M NaCl. The 1 ml fractions were assayed for activity and purity measured by 12.5% SDS-PAGE and pooled accordingly. The Mono S pool was dialyzed overnight at 4° C. versus 1 liter of Final Storage Buffer (20 mM Kpi, pH 6.5, 1.0 mM DTT, and 50% glycerol).

The protein concentration was determined by the Bradford Protein Assay (BioRad, Hercules, Calif.). The calculated DNA polymerase specific activity for the rBst exo-fragment was approximately 150,000 U/mg. Using conventional lyophilization techniques, a solution containing the rBst exo- fragment may be lyophilized for storage. Preferably, the lyophilization solution includes one or more stabilizing agents such as an albumin, trehalose, maltitol, sucrose, sorbitol and ficoll. Typically, the lyophilization solution is aqueous. However, for prolonged storage at low temperatures, all or part of the solvent in the lyophilization solution may be glycerol.

EXAMPLE 7

Characterization of *B. stearothermophilus* DNA Polymerase I Exonuclease Activities The purity and molecular weight of the *B. stearothermophilus* DNA polymerase exo- fragments and the rBca exo-fragment was estimated by SDS-polyacrylamide gel electrophoresis (i.e., SDS-PAGE) using the Pharmacia PhastSystem (Piscataway, N.J.). FIG. 8 photographically depicts the purity of purified native *Bacillus stearothermophilus* holoenzyme (nBst holo), native *Bacillus stearothermophilus* exo- fragment (nBst exo-), recombinant *Bacillus stearothermophilus* exo- fragment (rBst exo-), and commercially available recombinant *Bacillus caldotenax* exo- fragment (rBca exo-, PanVera, Madison, Wis.) on a 20.0% SDS-PAGE gel stained with silver. In FIG. 8, Lanes 1–6 contain the following polypeptides: Lane 1, Low Molecular Weight Markers; Lane 2, nBst holo; Lane 3, nBst exo-; Lane 4, rBst exo-; Lane 5, rBca exo-; and Lane 6, Low Molecular Weight Markers.

Assays were performed to determine intrinsic/extrinsic exonuclease, endonuclease, and DNAse activities of the native Bst exo- fragment, recombinant Bst exo- fragment and for recombinant *B. caldotenax* exo- fragment (PanVera, Madison, Wis.). The protocols are described below and the results are summarized in TABLE 3A.

A 3'–5' exonuclease activity assay was performed in a final volume of 10 µl containing 50 mM Tris-HCl, pH 7.6, 10 mM MgCl$_2$, 1 mM DTT, 0.15 µg of [3'-$^3$H] dCTP and dGTP labelled λDNA/Taq I fragments and 5, 10 and 20 units of enzyme. Each sample was overlaid with 10 µl of light mineral oil and incubated at 60° C. for 1 hour. The reaction was terminated by the addition of 50 µl yeast t-RNA and 200 µl of 10% TCA. After incubation for 10 minutes on ice, the samples were centrifuged for 7 minutes in a microcentrifuge. Supernatant (200 μl) was removed and added to 6 ml of scintillation fluid and counted in a scintillation counter. The results are presented in TABLE 3A as the slope of the %-label released per unit of enzyme. An average of about 5800 cpm per sample was observed for the Bst exo- fragments compared to about 180 cpm per sample for the rBca exo- fragment.

A 5'–3' assay was performed in a manner identical to the 3'–5' exonuclease assay, except for the use of [5'-$^{32}$p] λ DNA/HaeIII fragments as substrate. Double-stranded and single stranded DNAse assays were performed using the protocol for the 3'–5' exonuclease assay, except for the use of [$^{32}$p] λ DNA as substrate. The DNA was treated for 3 minutes at 100° C. and immediately chilled on ice prior to assaying for single stranded DNAse activity.

An assay for endonuclease activity was performed in a final volume of 10 μl containing: 50 mM Tris-HCl, pH 7.6, 10 mM MgCl$_2$, 1 mM β-mercaptoethanol, 0.5 μg pBR322, and 5, 10 or 20 units of enzyme. Each sample was overlaid with 10 μl of light mineral oil and incubated at 60° C. for 1 hour. Two microliters of 0.25% bromophenol blue, 1 mM EDTA, and 40% sucrose was added to stop the reaction. After a short centrifugation, 6 μl of the bottom layer was removed and electrophoresed on 1.5% agarose gels in 1X TBE. The mobility change from the supercoiled to the linear form of pBR322 was recorded.

TABLE 3A

Contamination levels of nBst, rBst and rBca exo- fragments as slope of %-release/unit of enzyme

| Enzyme | 3'-5' exo-nuclease | 5'-3' exo-nuclease | ss DNAse | ds DNAse | Endo-nuclease |
|---|---|---|---|---|---|
| nBst exo- | 0.0 | 0.06 | 0.0 | 0.0 | 0.0 |
| rBst exo- | 0.0 | 0.0 | 0.0 | 0.0 | 0.0 |
| rBca exo- | 0.0 | 0.3 | 0.0 | 0.05 | 0.0 |

EXAMPLE 8

Comparison of the Polymerase Activities Of *B. stearothermophilus* and *B. caldotenax* DNA Polymerases Biological properties of native *B. stearothermophilus* DNA pol I exo- fragment (nBst exo-, lot #30419; CHIMERx, Inc., Cat. No. 1112-01, Madison, Wis.); recombinant *B. stearothermophilus* exo- fragment (rBst exo-) purified from *E. coli* [pPEK 5]; and recombinant *B. caldotenax* exo- fragment (rBca exo-, PanVera Inc., Madison, Wis.) were compared using a number of protocols described below.

The molecular weights and purities of the preparations of the various enzymes were estimated by acrylamide gel electrophoresis utilizing the Pharmacia PhastSystem (Piscataway, N.J.) for electrophoresis and silver staining. A comparison of the apparent molecular weights estimated from 12.5% and 20.0% acrylamide gels and the calculated molecular weights derived from available sequence data is given in TABLE 3B. A purity of greater than 90% was estimated for the native and recombinant Bst exo- fragments and less than 80% estimated for the rBca exo- fragment analyzed.

TABLE 3B

| | Apparent Mol. Weight | | Calculated |
|---|---|---|---|
| Enzyme | 12.5% gel | 20.0% gel | Mol. Weight |
| nBst exo- | 65 kD | 65 kD | n/d |
| rBst exo- | 65 kD | 65 kD | 65 kD |
| nBca exo- | 65 kD | 65 kD | 65 kD |

Using the Pharmacia PhastSystem, the polymerases and standards were subjected to isoelectric focusing. The experimentally derived pI values of the samples were compared to values calculated from derived amino acid sequence information. The results are given in TABLE 4.

TABLE 4

| | pI Values | |
|---|---|---|
| Enzyme | Calculated pI | Measured pI |
| nBst exo- | n/d | 5.4 |
| rBst exo- | 5.4 | 5.6 |
| rBca exo- | 5.4 | 5.3 |

The relative DNA polymerase activities of the enzymes were assayed at 60° C. at different pH values. The pH of selected buffers were adjusted at 23° C., to permit direct comparison to published results. TABLE 5A shows the measured pH values at 60° C. for 1× buffers which were titrated at 23° C. Unless otherwise indicated, pH values reported herein were adjusted at about 23° C.

TABLE 5A

Change of pH as a function of temperature

| # | Buffer | pH at 23° C. | pH at 60° C. |
|---|---|---|---|
| 1. | PIPES-NaOH | 6.0 | 5.5 |
| 2. | PIPES-NaOH | 6.5 | 6.0 |
| 3. | Tris-HCl | 7.5 | 6.4 |
| 4. | Tris-HCl | 8.0 | 7.0 |
| 5. | Tris-HCl | 8.5 | 7.4 |
| 6. | Tris-HCl | 9.0 | 8.0 |
| 7. | Tris-HCl | 9.5 | 8.6 |
| 8. | Triethylamine-HCl | 9.5 | 8.9 |
| 9. | Triethylamine-HCl | 10.0 | 9.15 |

The activity assays were performed in a 100 μl (final volume) reaction mixture, containing 0.1 mM dCTP, dTTP, dGTP, [α$^{33}$P]dATP, 0.3 mg/ml activated calf thymus DNA and 0.5 mg/ml BSA in a set of buffers containing: 50 mM KCl, 1 mM DTT, 10 mM MgCl$_2$ and 50 mM of one of three buffering compounds: PIPES, Tris or Triethylamine. A dilution to 0.1 units/μl of each polymerase enzyme were prepared, and 5 μl of these dilutions was added to the reaction mixture, followed by incubation at 60° C. for 10 minutes Independent experiments were performed and curves constructed. FIG. 3 graphically depicts the relative activities of the enzymes studied, calculated as the ratio of counts per minute (corrected for background and enzyme dilution) at a given pH to counts per minute at the maximum value for that enzyme. The optimal ranges (>90% activity) for the three enzymes tested are provided in TABLE 5B.

TABLE 5B

| Optimal pH Range (as titered at 23° C.) | |
|---|---|
| Enzyme | pH |
| nBst exo- | 7.0–10.0 |
| rBst exo- | 7.0–10.0 |
| rBca exo- | 7.0–10.0 |

These values are about 1 pH unit higher than for buffers measured at 60° C. (see TABLE 5A).

The pH protocol described above was modified to determine the influence of $MgCl_2$ concentration on the activities of the DNA polymerases. The reaction buffers included 50 mM Tris-HCl pH 8.3 (23° C.) and $MgCl_2$ concentrations from 0.0 to 20.0 mM. Independent experiments were performed and curves were constructed (FIG. 4) showing the relative activity of nBst exo- fragment, rBst exo- fragment, and rBca exo- fragment. The optimal activity for all three enzymes is at a 1.0 mM $MgCl_2$ final concentration.

The above protocol was modified to determine the influence of $MnCl_2$ concentration on the activities of the DNA polymerases (in the absence of magnesium ions). The reaction buffers included $MnCl_2$ concentrations from 0.0 to 5.0 mM. Due to the precipitation of oxidation products ($MnO_2$) of $MnCl_2$, the $MnCl_2$ solution was prepared just prior to the assay. Independent experiments were performed and a curve was constructed (FIGURE 5a) showing relative activity of the enzymes. The optimal activities for the native Bst, recombinant Bst exo- fragment and recombinant Bca exo- fragments were at 0.5 mM $MnCl_2$.

The temperature optima of the polymerase enzymes (nBst exo-, rBst exo- and rBca exo-) were determined by incubating 1.0 unit of enzyme for 10 minutes at 37°, 50°, 60°, 65°, 70°, 75°, and 80° C., in a 100 µl DNA polymerase activity assay as described previously. FIG. 6 depicts the percent relative polymerase activity, calculated as described above, as a function of temperature. As reflected in FIG. 6, the temperature optima was 70° C. for all three enzymes; whereas at 80° C. there was approximately 20% of activity remaining.

EXAMPLE 9

Comparison of Reverse Transcriptase Activity of the DNA Polymerase Enzymes

The RNA dependant DNA polymerase (reverse transcriptase, R.T.) activities of native and recombinant Bst exo- fragments and the recombinant Bca exo- fragment were compared. After a determination of the $MnCl_2$ optima for each enzyme (FIG. 5b), 1.0 unit of enzyme was compared in R.T. assays with either a Poly rA:$dT_{50}$ or mRNA substrate. In this assay, product quantity was determined by glass filter precipitation as previously described, and product quality by autoradiograph of a 1.2% TBE agarose gel containing reaction products.

A.

Using a modification of a procedure described by Meyers, T. W. and Gelfand, D. H., Biochemistry 30: 7661–7666 (1991), the reverse transcriptase activity of the native and recombinant Bst exo- fragments and the recombinant Bca exo- fragments were compared in the presence of 0 mM to 5.0 mM $MnCl_2$. The reaction (50 µl) contained 1× Reaction Buffer (50 mM Tris-HCl, pH 8.6, 100 mM KCl), 1.0 mM DTT, 0.2 mM PolyA:$dT_{50}$, 0.5 mM [3'-$^3$H] dTTP (80 µCi/ml), 0.5 units enzyme, and the balance $H_2O$. The reaction mix without enzyme was preincubated at 50° C. for 1 minute prior to enzyme addition. The reaction was incubated at 50° C. for 10 minutes after which 40 µl was removed and filter precipitated as previously described. As seen in FIGURE 5b, the $MnCl_2$ optima for all three enzymes is 1.0 mM. Also, the ratio of RNA dependant RNA polymerase to DNA dependant DNA polymerase was about 1.4 and 2.0 for native and recombinant Bst exo- fragments respectively, and about 0.8 for the recombinant Bca exo- fragment.

B.

A variation of the assay described above at 1.0 mM $MnCl_2$ was used to compare quantity and quality of R.T. activities using 1.0 unit of each enzyme by filter precipitation and autoradiography respectively. A 15 µl sample was removed after 1 hour of incubation at 50° C. for filter precipitation as previously described. Another 15 µl sample was remove and mixed with 5 µl of stop solution (95% deionized formamide, 10 mM EDTA, 0.05% xylene cyanole FF, 0.05% bromophenol blue) and loaded onto a 1.2% TBE agarose gel along with 0.5 µg of [$\gamma^{33}$P] labelled 1 kb Perfect Ladder (CHIMERx) and electrophoresed at 100 volts for approximately 2 hours. The gel was then dried in a Lab-Conco gel drier for 30 minutes. The dried gel was then autoradiographed at −70° C. for 3 days and developed to visualize bands.

Messenger RNA was isolated from approximately 1.0 gram of hybridoma cells (Ausubel et al., Current Protocols in Molecular Biology, Greene Publishing Associates and John Wiley & Sons, New York (1990)). The following substitutions in the above assay described in Example 9A were made; 1.0 µg of mRNA primed with 0.5 mM Oligo $dT_{50}$ (SuperTech, Bethesda, Md.) for PolyrA:$dT_{50}$ and 0.5 mM mixed dNTPs with 0.05 mCi/ml [$\alpha^{33}$P] dATP for [3'-$^3$H] dTTP. When using polyrA:$dT_{50}$ as substrate the only substitution was 5 mM [$\alpha^{32}$P] dTTP for [3'-$^3$H] dTTP. Precipitable counts minus background for each enzyme with each substrate are shown in TABLE 6. As seen in FIG. 7 both the native and recombinant Bst exo- fragments show an increase in product quantity and length as compared to products made by the recombinant Bca exo- fragment.

TABLE 6

| Comparison of R.T. net precipitable counts per minute | | |
|---|---|---|
| Enzyme | Poly rA:$dT_{50}$ | mRNA |
| nBst exo- | 2,421 cpm | 837,037 cpm |
| rBst exo- | 2,941 cpm | 691,545 cpm |
| rBca exo- | 2,001 cpm | 430,418 cpm |

EXAMPLE 10

DNA Sequencing Using nBst, rBst and rBca Exo-Fragments

Native and recombinant Bst exo- fragment and recombinant Bca exo- fragment (PanVera, Madison) were tested for their performance in DNA sequencing with internal labelling using ssDNA and dsDNA template by substituting nBst exo-, rBst exo- or rBca exo- in the Bst DNA Sequencing Kit (BioRad, Hercules, Calif.).

A.

The ssDNA sequencing reactions for the native and recombinant Bst exo- fragments and the recombinant Bca exo-fragment were performed using 5.0 units of enzyme. Briefly, a reaction cocktail (12 µl) was prepared containing 2.0 µl ssM13mp18 DNA (approx. 0.4 µg), 5.0 µl 5× Bst Sequencing Reaction buffer (100 mM Tris-HCl, pH 8.6, 100 mM MgCl$_2$), 1.0 µl [α$^{33}$P]-dATP (10 mCi/ml), 5.0 units of enzyme (2.0 µl of a 2.5 unit/µl solution) and balance H$_2$O. Four d/ddNTP mixtures were also prepared (A mix: 0.62 µM dATP, 62 µM dCTP, 62 µM dGTP, 62 µM dTTP, 25 µM ddATP; C mix: 0.8 µM dATP, 8 µM dCTP, 80 µM dGTP, 80 µM dTTP, 50 µM ddCTP; G mix: 0.8 µM dATP, 80 µM dCTP, 4 µM dGTP, 80 µM dTTP, 75 µM ddGTP; T mix: 0.8 µM dATP, 80 µM dCTP, 80 µM dGTP, 8 µM dTTP, 150 µM ddTTP). The sequencing reactions were performed by mixing 2.5 µl of reaction cocktail with 2 µl of the appropriate pre-incubated d/ddNTP mixture and incubating at 65° C. for 2 minutes. After this incubation, 2 µof 1× Chase Solution (0.5 mM each dNTP) was added, gently mixed and the reaction allowed to incubate for an additional 2.0 minutes. The reaction was terminated by adding 4.0 µl of stop solution (95% deionized formamide, 10 mM EDTA, 0.05% xylene cyanole FF, 0.05% bromophenol blue) and placing the reaction on ice.

The reactions were heated at 90° C. for 3 minutes just prior to loading onto a 6% sequencing gel. Two microliters of each sample was loaded and electrophoresed at 2000 volts for 1.5 hours. The gel was autoradiographed and analyzed. FIG. 9A photographically depicts a portion of a sequencing gel showing the same DNA sequence for all enzymes used. Very little background was observed with all three enzymes and an increase in intensity was seen with the Bst enzymes.

B.

The utility of recombinant Bst exo-fragment and native Bst exo- fragment for sequencing with internal labeling using double-stranded DNA template was demonstrated in a sequencing reaction in which a [α$^{33}$P]-dATP labeling protocol and double stranded pUC19 template were used.

To promote efficient priming, 2 ug (18 µl) of pUC19 double-stranded DNA template was denatured by adding 2 µl of 2M NaOH, and incubating for 5 minutes at room temperature. The reaction was neutralized by adding 2 µl of 2M sodium acetate, pH 4.6, precipitated, 70% EtOH washed, air-dried, and resuspended in 7 µl deionized water. In addition, reaction cocktails without enzyme were heated to 70° C. for 10 minutes then allowed to cool at room temperature for 10 minutes.

For each enzyme, a 12 µl extension/labeling sequencing reaction was performed in the same manner as described in EXAMPLE 10A except for 2 µg denatured pUC18 dsDNA in substitution for M13mp18 ssDNA.

Each reaction was heated at 90° C. for 3 minutes immediately prior to loading 2 µl onto a 6.0% sequencing gel. Results are depicted in FIG. 9b. Greater than 150 bases of readable pUC18 sequence with little background is seen.

EXAMPLE 11

Comparison of the Processivity of DNA Polymerase Enzymes

Using a modification of a procedure described by Tabor et al., *J. Biol. Chem.* 262: 16212–16223 (1987), the processivity of the native and the recombinant Bst exo- fragments, and recombinant Bca exo- fragment were compared. The "processivity" of a DNA polymerase enzyme is a measure of the rate at which the enzyme moves forward along a template while catalyzing DNA synthesis, i.e., a measure of the speed at which DNA polymerization takes place in the presence of the enzyme.

To prepare the assay, a 50 µl reaction cocktail was prepared with 2.5 µg M13 mp18 ssDNA, 10 µl ddATP mix (20 µM dATP; 60 µM each of dCTP, dGTP, and dTTP; 300 µM ddATP), 2.5 µl γ$^{33}$P labelled forward sequencing primer (3 µg/µl), 10 µl 5× reaction buffer (100 mM Tris-HCl, pH 8.6; 100 mM MgCl$_2$), balance H$_2$O. Additionally, dilutions of the native and recombinant Bst exo- fragments, and the rBca exo- fragment were prepared with dilution buffer described in EXAMPLE 1 to create enzyme solutions of 0.25 and 0.025 units/mi.

To perform the assay, 7.0 µl of the reaction cocktail were mixed with 2.0 µl of diluted DNA polymerase enzyme. The addition of 0.5 or 0.05 units of exo- fragment per reaction yields approximately 1:100 and 1:1000 enzyme molecule: template molecule ratios respectively. The use of such low polymerase concentrations minimizes the "bumping off" from template by competing polymerase molecules. Reaction mixtures were incubated at 65° C. and 2 µl samples were removed after 1.0, 3.0 and 6.0 minutes. Reactions were stopped by adding 1.0 µl stop buffer (EDTA/DTT/BromoPhenol Blue/xylene cyanol), heated at 90° C. for 3 minutes and loaded onto a 6% polyacrylamide sequencing gels. The gel was electrophoresed for approximately 2 hours and autoradiographed at −70° C.

In this assay, a highly processive DNA polymerase enzyme produces strong, slow-mobility (larger) labelled bands on an autoradiograph, whereas a less processive DNA polymerase produces higher-mobility (smaller) fragments and/or bands with less intensity. As seen in FIG. 10, the lanes designated with an arrow, corresponding to 6.0 minutes of incubation at a 1:1000 enzyme to substrate ratio were used to determine processivity. FIG. 10 shows that rBca exo-produced no visible high molecular weight species in the slowest half of the electrophoretogram. In contrast, the nBst exo- fragment produced more species of both higher and lower molecular weight than did rBca exo-. Further, FIG. 10 reflects that the rBst exo- fragment exhibited the greatest production of the slower moving high molecular weight DNA molecules. The rBst exo- fragment also produced more of the faster moving lower molecular weight DNA molecules than did rBca exo-. In terms of processivity, rBst exo->>rBca exo- and rBst exo->nBst exo-. Based upon FIG. 10, the comparative processivity from increasing to decreasing order was as follows: recombinant Bst exo->nBst exo->rBca exo-. Thus, the rBst exo- fragment (amino acid residues 285–876 of SEQ ID NO: 2) of the present invention exhibited the greatest processivity of the three exo- fragments tested.

EXAMPLE 12

Thermophilic Strand Displacement Amplification Using Recombinant *B. stearothermophilus* exo-Fragment Recombinant Bst exo- fragment was tested for its functional ability in thermophilic strand displacement amplification (SDA) essentially as described by Walker, T. G. *Emperical Aspects of Strand Displacement Amplification*, Becton Dickenson Research Center, Cold Spring Harbor Laboratory Press, Cold Spring Harbor, N.Y. (1993). The SDA methodology is also disclosed in U.S. Pat. No. 5,270,184. Improved SDA methods are disclosed in U.S. Pat. Nos. 5,270,252 and 5,455,166. The disclosures in each of these three patents, as related to SDA methodology, is incorporated herein by reference.

Target plasmid, pSK4.3, containing the IS6110 region of Mycobacterium tuberculosis obtained from G. T. Walker, Becton Dickenson, Research Triangle Park, N.C.) was digested with Xba I (MBR, Milwaukee, Wis.) and serially diluted in human placental DNA (Sigma). SDA was performed in 50 μl reactions containing $1\times10^6$ copies of target plasmid DNA, 500 ng of human placental DNA, 160 units BsoB I (New England Biolabs,), 8 units of recombinant Bst exo- DNA polymerase, 1.4 mM each dCTPαS, dTTP dGTP, dATP (Pharmacia, Milwaukee, Wis.), 35 mM $K_2PO_4$ pH 7.6, 0.1 mg/ml non-acetylated BSA, 3 mM Tris-HCl, 10 mM $MgCl_2$, 11 mM NaCl, 0.3 mM DTT, 4 mM KCl, 4% glycerol, 0.008 mM EDTA, 500 nM of primers S1 and S2 and 50 nM of primers B1 and B2 (the KCl, glycerol and EDTA are contributed by the BsoB I storage buffer). Prior to the addition of BsoB I and the rBst exo- DNA polymerase, incomplete samples (35 μl) were denatured by heating for 3 minutes at 100° C. followed by 3 minutes at 60° C. for primer annealing. BsoB I and Bst DNA polymerase were diluted together to 10.7 units/μl and 0.53 units/μl, respectively, in 15 μl of New England Biolabs Buffer (10 mM Tris-HCl pH 7.9, 10 mM $MgCl_2$, 50 mM NaCl, 1 mM DTT). SDA proceeded for 20 minutes at 60° C. Amplification was terminated by heating for 5 minutes at 100° C. A non-SDA control was created by heating a sample in a boiling water bath immediately after enzyme addition.

Following SDA, amplified products were detected by DNA polymerase extension of [γ-$^{32}$P]-labelled detector probe hybridized to the central region of the amplified IS6110 target sequence. Five microliters from each completed SDA reaction were added to 5 μl of a reaction mixture containing 47 mM $K_2PO_4$ pH 7.6, 0.2 mM each dATP, dCTP, dGTP and dTTP, 7 mM $MgCl_2$, 0.1 mg/ml BSA and 0.1 μM [γ-$^{32}$P]-labelled detector probe. The samples were heated for 2 minutes at 100° C. followed by 2 minutes at 37° C. The detector probe was extended to a diagnostic length by the addition of 1.0 μl (9 units) of exo-Klenow polymerase (MBR, Milwaukee, Wis.) and incubation at 37° C. for 15 minutes. Eleven microliters of a denaturing stop solution (95% deionized formamide, 10 mM EDTA, 1 mM DTT, 0.05% bromophenol blue/xylene cyanol) was added and 11 μl of each resultant sample was analyzed by denaturing gel electrophoresis and autoradiograph on Kodak X-ARS film for 3 hours. (See FIG. 11). As depicted in FIG. 11, amplified product is seen at 59 and 40 bp in the presence of active rBst exo- fragment ("rBst exo-") with undetectable background in the negative control ("-C"). Thus, the rBst exo- fragment of the present invention exhibited utility in thermophilic SDA.

EXAMPLE 13

Large-Scale Purification of Recombinant Bst exo- Fragment

Thirty-five grams of *E. coli* [pPEK 5] were thawed in 150 ml of lysis buffer (20 mM Tris-HCl pH 8.0, 0.5 mM EDTA, 50 mM NaCl, 1 mM DTT, 0.02% Brij-35, 10 mM $MgCl_2$, 0.1 mg/ml lysozyme, and 1.0 mM phenylmethylsulfonylflouride). The cell suspension was allowed to stir at 4° C. for 60 minutes. The homogenous suspension was sonicated for six, 30 second bursts with 30 seconds of cooling between each burst. The lysate was then heated to 65° C. for 15 minutes to denature the non-thermostable proteins and then cooled on ice for 15 minutes. After centrifugation at 9000 rpm for 60 minutes to remove cell debris and denatured proteins, the supernatant was filtered through a 0.8/0.2 μm filtration unit and applied to a Pharmacia 10×10 prepacked Mono Q column equilibrated in Buffer A: 20 mM Tris-HCl, pH 8.0, 1.0 mM DTT, 0.1 mM EDTA, 10 mM $MgCl_2$, and 0.02% Brij-35. After washing with 100 ml of Buffer A, the enzyme was eluted with a 90 ml linear gradient of Buffer A versus Buffer A at 0.4M NaCl. The 1 ml fractions were assayed for activity and pooled accordingly.

The Mono Q pool was dia-filtrated using a 30 kD (cutoff) membrane with Buffer A at pH 6.0 to concentrate and exchange the Buffer to Mono S loading conditions (Buffer A at pH 6.0 and conductivity at less than 10 mmhos). The pool was then applied to a Pharmacia 5×5 prepacked Mono S column equilibrated in Buffer A at pH 6.0. After washing with 20 ml of equilibration buffer, the enzyme was eluted with a 90 ml linear gradient of Buffer A, pH 6.0 to Buffer A, pH 6.0 at 0.3M NaCl. The 1 ml fractions were assayed for activity and purity was measured by 12.5% SDS-PAGE and pooled accordingly. The Mono S pool was dialyzed overnight a 4° C. versus 20 volumes of Final Storage Buffer (20 mM potassium phosphate, pH 6.5, 1.0 mM DTT, and 50% glycerol).

The protein concentration was determined by the Bradford Protein Assay (BioRad, Hercules, Calif.). The calculated DNA polymerase specific activity for the rBst exo- fragment was approximately 150,000 U/mg.

TABLE 7

| Enzyme | Quantity of Cells | Specific Activity (Units/mg protein) | Yield (Units/g cells) |
| --- | --- | --- | --- |
| nBst exo- | 500 g | 50,000 U/mg | 1000 U/g |
| rBst exo- | 35 g | 150,000 U/mg | 130,000 U/g |

The biological activities of the recombinant enzyme purified by the above-described protocol were analyzed using the assays described in preceding Examples. In the endonuclease activity assay described in Example 9, five, ten, and twenty unit challenges resulted in less than 5.0% conversion of supercoiled pBR322 to the linear form. The results of other assays described in EXAMPLE 9 are summarized in TABLE 8:

TABLE 8

Biological activities of recombinant Bst exo- fragment

| ASSAY | Activity rBst exo- |
| --- | --- |
| ds DNAse | 0% slope/unit |
| ss DNAse | 0% slope/unit |
| 3' Exonuclease | 0.06% slope/unit |
| 5' Exonuclease | 0% slope/unit |

Deposit of Biological Materials: The following plasmids have been deposited with the American Type Culture Collection (ATCC), 12301 Parklawn Dr., Rockville Md. 20852 (USA) pursuant to the provisions of the Budapest Treaty:

| Designation | Deposit Date | ATCC No. | Host Strain |
| --- | --- | --- | --- |
| pPEK 5 | | | DH5αF' |

Availability of the deposited materials is not to be construed as a license to practice the invention in contravention of the rights granted under the authority of any government in accordance with its patent laws.

The present invention has been described with reference to specific examples and embodiments. However, this application is intended to cover those changes and substitutions which, based on Applicants disclosure, are apparent and may be made by those skilled in the art without departing from the spirit and scope of the claims.

---

What is claimed is:

1. A purified and isolated DNA comprising the sequence set forth in SEQ ID NO: 1.

2. A purified and isolated DNA comprising nucleotides 1135 to 2946 of SEQ ID NO: 1.

3. The DNA of claim 2, further comprising nucleotides 316 to 1134 of SEQ ID NO: 1.

4. A vector wherein the DNA of claim 3 is operably linked to a promoter.

5. A cDNA consisting of nucleotides 1135 to 2946.

6. Plasmid pPEK 5.

7. A host cell transformed with a DNA having an expressible portion selected from nucleotides 316 to 2946 of SEQ ID NO: 1 and nucleotides 1135 to 2946 of SEQ ID NO: 1.

8. The host cell of claim 7, wherein said host cell is capable of expressing a thermostable polypeptide encoded by said DNA, said polypeptide having DNA polymerase activity.

9. The host cell of claim 8, wherein said host cell is a prokaryotic cell.

10. The host cell of claim 9, wherein said host cell is an *E. coli* cell.

11. An expression vector comprising a promoter operably linked to nucleotides 1135 to 2946 of SEQ ID NO: 1.

12. The expression vector of claim 10 having at least one insert comprising nucleotides 1135 to 2946 of SEQ ID NO: 1.

13. A purified fragment of *Bacillus stearothermophilus* DNA polymerase I protein comprising the sequence set forth in SEQ ID NO: 2.

14. The fragment of claim 13 being rBst exo-.

15. A purified fragment of *Bacillus stearothermophilus* DNA polymerase I protein encoded by the insert of plasmid pPEK 5.

16. The purified fragment of claim 15 wherein the fragment has a DNA polymerase activity between 50,000 U/mg protein and 500,000 U/mg protein.

17. A isolated and purified thermostable and recombinant polypeptide having DNA polymerase activity, said polypeptide comprising the amino acid sequence of SEQ ID NO: 2.

18. A recombinant polypeptide having a sequence comprising amino acid residues 274 to 876 of SEQ ID NO: 2.

19. The polypeptide of claim 18 in lyophilized form.

20. The polypeptide of claim 18 in solution form.

21. A method for thermocyclic amplification of nucleic acid comprising the following steps:

(a) contacting a nucleic acid with a thermostable recombinant polypeptide having amino acid residues 274 to 876 of SEQ ID NO: 2 under conditions suitable for amplification of said nucleic acid: and (b) amplifying said nucleic acid.

22. The method of claim 21 wherein the thermocyclic amplification of DNA is performed by Strand Displacement Amplification.

23. The method of claim 21 wherein thermocyclic amplification of DNA is performed by the Polymerase Chain Reaction.

* * * * *